US012662403B2

(12) United States Patent
Custelcean et al.

(10) Patent No.: US 12,662,403 B2
(45) Date of Patent: Jun. 23, 2026

(54) PHOTOSWITCHABLE GUANIDINIUM COMPOUNDS FOR REMOVAL OF OXYANIONS FROM LIQUID SOLUTIONS

(71) Applicant: UT-Battelle, LLC, Oak Ridge, TN (US)

(72) Inventors: Radu Custelcean, Beavercreek, OH (US); Bruce A. Moyer, Oak Ridge, TN (US); Jeffrey Einkauf, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 875 days.

(21) Appl. No.: 17/875,767

(22) Filed: Jul. 28, 2022

(65) Prior Publication Data

US 2023/0053638 A1 Feb. 23, 2023

Related U.S. Application Data

(60) Provisional application No. 63/226,778, filed on Jul. 29, 2021.

(51) Int. Cl.

*C02F 1/54* (2023.01)
*C02F 101/10* (2006.01)
*C07D 213/53* (2006.01)

(52) U.S. Cl.

CPC .............. *C02F 1/54* (2013.01); *C07D 213/53* (2013.01); *C02F 2101/101* (2013.01); *C02F 2303/16* (2013.01)

(58) Field of Classification Search

CPC ............... C07D 213/53; C02F 2303/16; C02F 2101/101; C02F 1/54
See application file for complete search history.

(56) References Cited

U.S. PATENT DOCUMENTS

| | | | | |
|---|---|---|---|---|
| 3,328,414 A * | 6/1967 | Bander | C07D 213/53 546/332 |
| 10,253,002 B2 * | 4/2019 | Page | C07D 333/58 |
| 11,001,554 B2 | 5/2021 | Williams et al. | |
| 11,040,296 B2 | 6/2021 | Brigham et al. | |
| 11,369,944 B2 | 6/2022 | Jansone-Popova | |

FOREIGN PATENT DOCUMENTS

WO WO-2014176636 A1 * 11/2014 ............. A01N 43/54

OTHER PUBLICATIONS

F. J. Barragan de la Rosa, Derivatives of carbohydrazide, thiocarbohydrazide, and diaminoguanidine as photometric analytical reagents I. 1,3-Bis[(2-pyridyl)methyleneamino]thiourea and 1,3-bis[(2-pyridyl)methyleneamino]guanidine, 1983, Talanta, vol. 30 edition 8, 555-564 (Year: 1983).*

* cited by examiner

*Primary Examiner* — Amber R Orlando
(74) *Attorney, Agent, or Firm* — Scully, Scott, Murphy & Presser, P.C.

(57) ABSTRACT

A compound having the following structure:

(1)

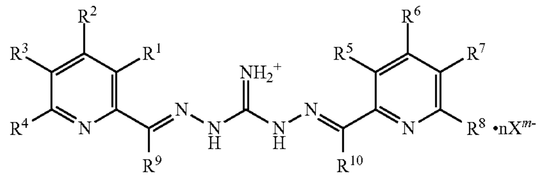

wherein: $R^1$, $R^2$, $R^3$, $R^4$, $R^5$, $R^6$, $R^7$, $R^8$, $R^9$, and $R^{10}$ are independently selected from (i) hydrogen atom, (ii) hydrocarbon groups (R) containing 1-30 carbon atoms and optionally substituted with one or more fluorine atoms, (iii) —OR' groups, (iv) —NR'$_2$ groups, (v) —C(O)R' groups, and (vi) halogen atoms, wherein R' groups are independently selected from R groups and hydrogen atoms, and wherein the R group optionally includes a C(O), ether, or amino linkage; $X^{m-}$ is an anionic species with a magnitude of charge m, where m is an integer of at least 1; and n is a number, provided that n×m=1. Also described herein are methods for removing one or more oxyanions from a liquid source by use of the above compound or mono-pyridyl derivative thereof.

19 Claims, 12 Drawing Sheets
(10 of 12 Drawing Sheet(s) Filed in Color)

8A

8B

9A

9B

*E*,*E*-2PyDIG·OTf⁻, 0 kcal/mol

*Z*,*Z*-2PyDIG·OTf⁻, 1.14 kcal/mol

PHOTOSWITCHABLE GUANIDINIUM COMPOUNDS FOR REMOVAL OF OXYANIONS FROM LIQUID SOLUTIONS

CROSS REFERENCE TO RELATED APPLICATION

The present application claims benefit of U.S. Provisional Application No. 63/226,778, filed on Jul. 29, 2021, all of the contents of which are incorporated herein by reference.

STATEMENT REGARDING FEDERALLY SPONSORED RESEARCH

This invention was made with government support under Prime Contract No. DE-AC05-00OR22725 awarded by the U.S. Department of Energy. The government has certain rights in the invention.

FIELD OF THE INVENTION

The present invention generally relates to compositions useful for removing oxyanion species from liquid solutions, such as removal of sulfate, phosphate, nitrate, chromate, selenate, arsenate, rhenate, or molybdate from a liquid, and to methods for using such compositions in removing such species.

BACKGROUND OF THE INVENTION

Effective separation of highly hydrophilic anions (e.g., sulfate, phosphate, selenate, and chromate) from competitive or dilute aqueous solutions remains a major challenge, despite the tremendous progress in anion receptor chemistry over the past decade. This problem arises in numerous fields from radioactive contaminants in nuclear wastes to separation of ionic pollutants from groundwater. In the particular case of sulfate, although a significant number of sulfate-binding receptors have been reported (e.g., I. Ravikumar et al., *Chem. Soc. Rev.,* 41, 3077, 2012), they have shown limited success in the substantial removal of this anion from water. A significant obstacle in the development of anion receptors is often the expensive multi-step synthesis required for their assembly, which generally involves tedious purifications and the use of toxic reagents and solvents. Traditionally, ion stripping has relied on changes in chemical gradients, such as pH swings, which typically generate dilute streams of the separated ions and large amounts of secondary waste.

The removal of superhydrophilic anions, such as sulfate and phosphate, from brines, agricultural runoff, and industrial waste continues to be an ongoing challenge. Seawater, in particular, contains very high levels of sulfate (~3,000 mg/L), and seawater is used on a large scale in oil-field injection operations. During such operations, the sulfate in the seawater combines with strontium and barium found in rock to form barium and strontium sulfate scale. The precipitation of barium and strontium sulfates is highly detrimental to the process, such as by clogging lines and destroying production wells. The conventional technology for removing sulfate from seawater is by nanofiltration, which can reduce sulfate levels to about 50 mg/mL. However, some drawbacks to this approach are the remaining high sulfate levels, the need to pressurize the system to 20-30 bars, which results in a significant expenditure in energy, and membrane fouling. Other methods involve scale-removing chemicals, but these are known to be difficult to use and expensive, and moreover, they are not very effective against sulfate scales. Another technology, known as the MD-LPP process, yields sulfate-free seawater, but the process has the significant drawbacks of employing high pressures and pre-concentrating the seawater.

The difficulty in separating superhydrophilic anions, such as sulfate, from aqueous solutions can be attributed to their high free energies of hydration ($-1080$ kJ $mol^{-1}$ for sulfate) which makes their removal from aqueous solutions quite unfavorable in comparison to less hydrophilic anions (e.g., $-381$ kJ $mol^{-1}$ for chloride) (e.g., Y. Marcus, *J. Chem. Soc. Faraday Trans.,* 1991, 87, 2995). Nevertheless, targeted separation of superhydrophilic anions from aqueous solutions is necessary for a range of important water treatment applications, including processing of radioactive wastes, oil production, and desalination. In a conventional method for separation of aqueous sulfate, the anion is hydrogen-bonded by cationic precipitants that are added to the aqueous phase (e.g., R. Custelcean et al., *Angew. Chem. Ed. Int.,* 54, 10525 (2015) and R. Custelcean et al., *Chem. Eur. J.,* 22, 1997 (2016)). This process is driven by the favorable lattice formation energy, which compensates for the unfavorable ion desolvation energy.

Liquid-liquid extraction is a common approach to ion separation, where ions are transported from water into an immiscible aliphatic solvent. However, liquid-liquid extraction has so far proven difficult for separation of superhydrophilic anions, such as sulfate, because (1) selectivity of anion extraction into oil generally follows the Hofmeister series, which favors extraction of less hydrophilic anions; and (2) hydrophilic ions and receptor groups are inherently unstable in aliphatic oil because of retention of their hydration shells, thereby causing uncontrolled aggregation and phase transitions.

There would be a significant benefit in a removal process that could substantially remove superhydrophilic oxyanions, such as sulfate, from seawater or industrial waste by a straight-forward approach without the impediments and shortcomings of previous efforts. There would be a further benefit in such a method which also does not require chemical-based (often strongly alkaline) methods for stripping the anion from the extractant compound and simultaneously producing a neutral form of the extractant compound. There would a further benefit in such a method which also does not require chemical-based (often strongly acidic) methods for regenerating the cationic extractant compound from the neutral extractant compound.

SUMMARY OF THE INVENTION

The present disclosure describes a process for removing one or more types of oxyanions (e.g., sulfate, phosphate, or chromate) from a liquid source by contacting the liquid source with any one of a series of dipyridyl- or monopyridyl-iminoguanidinium compounds (i.e., oxyanion precipitating compounds) that are highly effective in complexing with and precipitating one or more of the oxyanions from the liquid source. The oxyanion precipitating compounds described herein can advantageously complex with and precipitate one or more oxyanions, such as sulfate, nitrate, selenate, phosphate, arsenate, carbonate, bicarbonate, or metal oxyanion (e.g., chromate or rhenate) in a liquid, in some cases selectively. The oxyanion precipitating compounds described herein can furthermore be made to release the captured oxyanion by non-chemical means, specifically, by exposing the compound-anion complex (i.e., "salt") to electromagnetic radiation to isomerize the open (E,E) compound of Formula (1) to a closed (Z,Z) form which can no longer bind to the anion. The process described herein is advantageously straight-forward, cost-efficient, and environmentally friendly while at the same time capable of removing a substantial portion or all of one or more oxyanions from a liquid source, in some cases highly selectively, even when the liquid source is highly dilute or contains a range of different anions.

In some embodiments, the oxyanion precipitating compounds has a dipyridyl-diiminoguanidinium structure as follows:

(1)

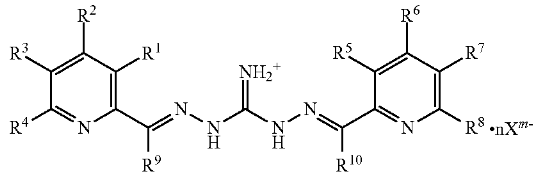

In Formula (1) above, $R^1$, $R^2$, $R^3$, $R^4$, $R^5$, $R^6$, $R^7$, $R^8$, $R^9$, and $R^{10}$ are independently selected from (i) hydrogen atom, (ii) hydrocarbon groups (R) containing 1-30 carbon atoms and optionally substituted with one or more fluorine atoms, (iii)—OR' groups, (iv)—$NR'_2$ groups, (v)—C(O)R' groups, and (vi) halogen atoms, wherein R' groups are independently selected from R groups and hydrogen atoms. The species $X^{m-}$ is an anionic species with a magnitude of charge m, where m is an integer of at least 1; and n is an integer of at least 1, provided that n×m=1. In some embodiments, $R^9$ and $R^{10}$ are hydrogen atoms and/or $R^1$, $R^2$, $R^3$, $R^4$, $R^5$, $R^6$, $R^7$, and $R^8$ are hydrogen atoms. In other embodiments, $R^1$, $R^2$, $R^3$, $R^4$, $R^5$, $R^6$, $R^7$, $R^8$, $R^9$, and $R^{10}$ are not all hydrogen atoms, such as wherein at least one of $R^1$, $R^2$, $R^3$, $R^4$, $R^5$, $R^6$, $R^7$, $R^8$, $R^9$, and $R^{10}$ is selected from R, —OR', —$NR'_2$, and —C(O)R'. Although the anion ($X^{m-}$) can be essentially any anion, including inorganic and organic anions, in particular embodiments, $X^{m-}$ is a halide, such as chloride, bromide, or iodide, or $X^{m-}$ is a pseudohalide or any oxygen-containing anion (i.e., oxyanion), such as any of those described above.

In other embodiments, the oxyanion precipitating compound selects at least one of $R^1$, $R^2$, $R^3$, $R^4$, $R^5$, $R^6$, $R^7$, and $R^8$ as an —OR' (alkoxide) group, and R' is independently selected from R groups and hydrogen atoms. In particular embodiments, the oxyanion precipitating compound has the following structure:

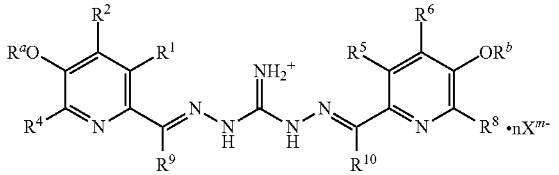

wherein $R^1$, $R^2$, $R^4$, $R^5$, $R^6$, $R^8$, $R^9$, and $R^{10}$ are as defined above, and $R^a$ and $R^b$ are linear or branched alkyl or alkenyl groups containing 1-30 carbon atoms.

In another aspect, the present disclosure is directed to a method for removing an oxyanion from a liquid source. In the method, the liquid source is contacted with an oxyanion precipitating compound, as described above, which results in precipitation of a salt of the oxyanion precipitating compound and oxyanion. The oxyanion precipitating compound can only bind to the anion when it is in the E,E ("open") form, as depicted in any of the above structures. In some embodiments, following precipitation of the salt, the salt is removed from the liquid source, transferred to a second liquid, and the salt is exposed to electromagnetic radiation (e.g., wavelength below 600 nm) in the second liquid to isomerize the compound of Formula (1) to a closed (Z,Z) form, which can no longer bind to the anion, thereby releasing the anion with simultaneous dissolution of an uncomplexed form of the closed oxyanion precipitating compound according to Formula (1') in the second liquid or in a third liquid in contact with the second liquid. Preferably, the released oxyanion is insoluble in the second liquid while the uncomplexed form of the closed oxyanion precipitating compound is soluble in the second liquid; or alternatively, a third liquid is in contact with and immiscible with the second liquid, wherein the released oxyanion is soluble in the second liquid while the uncomplexed form of the closed oxyanion precipitating compound is substantially more soluble in the third liquid than the second liquid, thereby separating the uncomplexed compound from the released anion. Thereafter, the uncomplexed form of the closed oxyanion precipitating compound may be thermally converted back to the E,E (open form) structure, and the E,E (open form) may be re-used in a subsequent process of removing an oxyanion from a liquid source.

BRIEF DESCRIPTION OF THE DRAWINGS

The patent or application file contains at least three drawings executed in color. Copies of this patent or patent application publication with color drawing(s) will be provided by the Office.

DETAILED DESCRIPTION OF THE INVENTION

Figure 1:
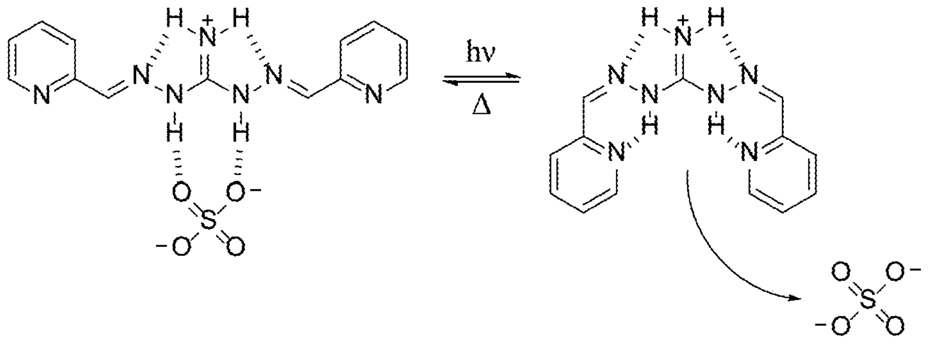
FIG. 1. Schematic showing structural changes and binding behavior in the photoswitching of the 2PyDIG cation and the corresponding sulfate anion binding and release upon irradiation with UV light. Hydrogen bonds are marked as dashed lines.

As used herein, the term "hydrocarbon group" (also denoted by the group R) is defined as a chemical group composed solely of carbon and hydrogen, except that the hydrocarbon group may (i.e., optionally) be substituted with one or more fluorine atoms to result in partial or complete fluorination of the hydrocarbon group. The hydrocarbon group (R) may, in some embodiments, include a carbonyl (—C(O)—) linkage, ether (—O—) linkage, or amino linkage (e.g., —NH— or —NR—). In different embodiments, one or more of the hydrocarbon groups can contain precisely, or a minimum of, or a maximum of, for example, 1, 2, 3, 4, 5, 6, 7, 8, 9, 10, 12, 15, 18, 20, 22, 24, 26, 28, or 30 carbon atoms, or a number of carbon atoms within a particular range bounded by any two of the foregoing carbon numbers. Hydrocarbon groups in different compounds described herein, or in different positions of a compound, may possess the same or different number (or preferred range thereof) of carbon atoms in order to independently adjust or optimize such properties as the complexing ability, extracting (extraction affinity) ability, or selectivity of the compound.

In a first set of embodiments, the hydrocarbon group (R) is a saturated and straight-chained group, i.e., a straight-chained (linear) alkyl group. Some examples of straight-chained alkyl groups include methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-eicosyl, n-docosyl, n-tetracosyl, n-hexacosyl, n-octacosyl, and n-triacontyl groups.

In a second set of embodiments, the hydrocarbon group (R) is saturated and branched, i.e., a branched alkyl group. Some examples of branched alkyl groups include isopropyl (2-propyl), isobutyl (2-methylprop-1-yl), sec-butyl (2-butyl), t-butyl (1,1-dimethylethyl-1-yl), 2-pentyl, 3-pentyl, 2-methylbut-1-yl, isopentyl (3-methylbut-1-yl), 1,2-dimethylprop-1-yl, 1,1-dimethylprop-1-yl, neopentyl (2,2-dimethylprop-1-yl), 2-hexyl, 3-hexyl, 2-methylpent-1-yl, 3-methylpent-1-yl, isohexyl (4-methylpent-1-yl), 1,1-dimethylbut-1-yl, 1,2-dimethylbut-1-yl, 2,2-dimethylbut-1-yl, 2,3-dimethylbut-1-yl, 3,3-dimethylbut-1-yl, 1,1,2-trimethylprop-1-yl, and 1,2,2-trimethylprop-1-yl groups, isoheptyl, isooctyl, and the numerous other branched alkyl groups having up to 20 or 30 carbon atoms, wherein the "1-yl" suffix represents the point of attachment of the group.

In a third set of embodiments, the hydrocarbon group (R) is saturated and cyclic, i.e., a cycloalkyl group. Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane).

In a fourth set of embodiments, the hydrocarbon group (R) is unsaturated and straight-chained, i.e., a straight-chained (linear) olefinic or alkenyl group. The unsaturation occurs by the presence of one or more carbon-carbon double bonds and/or one or more carbon-carbon triple bonds. Some examples of straight-chained olefinic groups include vinyl, propen-1-yl (allyl), 3-buten-1-yl ($CH_2$═CH—$CH_2$—$CH_2$—), 2-buten-1-yl ($CH_2$—CH═CH—$CH_2^-$), butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, 1,3,5-hexatrien-1-yl, 6-hepten-1-yl, ethynyl, propargyl (2-propynyl), 3-butynyl, and the numerous other straight-chained alkenyl or alkynyl groups having up to 20 or 30 carbon atoms.

In a fifth set of embodiments, the hydrocarbon group (R) is unsaturated and branched, i.e., a branched olefinic or alkenyl group. Some examples of branched olefinic groups include propen-2-yl ($CH_2$═C—$CH_3$), 1-buten-2-yl ($CH_2$═C—$CH_2$—$CH_3$), 1-buten-3-yl ($CH_2$═CH—CH—$CH_3$), 1-propen-2-methyl-3-yl ($CH_2$═C($CH_3$)—$CH_2^-$), 1-penten-4-yl, 1-penten-3-yl, 1-penten-2-yl, 2-penten-2-yl, 2-penten-3-yl, 2-penten-4-yl, and 1,4-pentadien-3-yl, and the numerous other branched alkenyl groups having up to 20 or 30 carbon atoms, wherein the dot in any of the foregoing groups indicates a point of attachment.

In a sixth set of embodiments, the hydrocarbon group (R) is unsaturated and cyclic, i.e., a cycloalkenyl group. The unsaturated cyclic group can be aromatic or aliphatic. Some examples of unsaturated cyclic hydrocarbon groups include cyclopropenyl, cyclobutenyl, cyclopentenyl, cyclopentadienyl, cyclohexenyl, cyclohexadienyl, phenyl, benzyl, cycloheptenyl, cycloheptadienyl, cyclooctenyl, cyclooctadienyl, and cyclooctatetraenyl groups. The unsaturated cyclic hydrocarbon group may or may not also be a polycyclic group (such as a bicyclic or tricyclic polyaromatic group) by either possessing a bond between two of the ring groups (e.g., biphenyl) or a shared (i.e., fused) side, as in naphthalene, anthracene, phenanthrene, phenalene, or indene fused ring systems.

In one aspect, the present disclosure is directed to specialized oxyanion precipitating compounds (i.e., oxyanion removing compounds) that have an ability to complex with an oxyanion and precipitate the oxyanion from a liquid source (i.e., liquid solution). The oxyanion can initially be dissolved in any suitable liquid phase (i.e., solvent). The solvent is typically water or an aqueous solution containing water and a water-soluble solvent (e.g., an alcohol, acetone, or DMF), but the solvent may be non-aqueous yet sufficiently polar for the oxyanion to remain dissolved.

The oxyanion precipitating compound contains a dipyridyl-iminoguanidinium moiety and has the following generic structure:

(1)

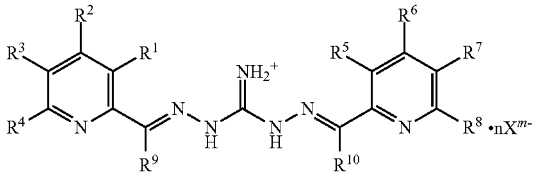

In Formula (1) above, $R^1$, $R^2$, $R^3$, $R^4$, $R^5$, $R^6$, $R^7$, $R^8$, $R^9$, and $R^{10}$ are independently selected from (i) hydrogen atom, (ii) hydrocarbon groups (R) containing 1-30 carbon atoms and optionally substituted with one or more fluorine atoms, as described above, (iii)—OR' groups, (iv)—NR'$_2$ groups, (v)—C(O)R' groups, and (vi) halogen atoms, wherein R' groups are independently selected from R groups and hydrogen atom. If one or more R groups are present in Formula (1), the one or more R groups may independently contain at least or more than 1, 2, 3, 4, 5, or 6 carbon atoms and up to, for example, 8, 10, 12, 15, 20, 25, or 30 carbon atoms, or any number of carbon atoms within a range bounded by any two of the foregoing values. In particular embodiments, the one or more R groups are independently selected from linear and branched alkyl groups. In some embodiments, one or both of $R^9$ and $R^{10}$ are hydrogen atoms. In other embodiments, one or both of $R^9$ and $R^{10}$ are not hydrogen atoms, or more particularly, selected from any of the groups (ii)-(vi) provided above. In some embodiments, one or more of (or all of) $R^1$, $R^2$, $R^3$, $R^4$, $R^5$, $R^6$, $R^7$, $R^8$, $R^9$, and $R^{10}$ are hydrogen atoms. In other embodiments, one, two, three, four, or more of (or all of) $R^1$, $R^2$, $R^3$, $R^4$, $R^5$, $R^6$, $R^7$, $R^8$, $R^9$, and $R^{10}$ are not hydrogen atoms, or more particularly, selected from any of the groups (ii)-(vi) provided above.

In a first set of embodiments, at least one of $R^1$, $R^2$, $R^3$, $R^4$, $R^5$, $R^6$, $R^7$, $R^8$, $R^9$, and $R^{10}$ (or at least one of $R^1$, $R^2$, $R^3$, $R^4$, $R^5$, $R^6$, $R^7$, and $R^8$) is an R group, or at least two, three, or four of $R^1$, $R^2$, $R^3$, $R^4$, $R^5$, $R^6$, $R^7$, $R^8$, $R^9$, and $R^{10}$ (or at least two, three, or four of $R^1$, $R^2$, $R^3$, $R^4$, $R^5$, $R^6$, $R^7$, and $R^8$) are R groups. If more than one R group is present, the R groups may be the same or different. In some embodiments, $R^1$, $R^2$, $R^3$, $R^4$, $R^5$, $R^6$, $R^7$, $R^8$, $R^9$, and $R^{10}$ (or $R^1$, $R^2$, $R^3$, $R^4$, $R^5$, $R^6$, $R^7$, and $R^8$) are selected from R groups and hydrogen atoms, and one or more additional groups selected from groups (iii)-(vi) may or may not be present.

In some embodiments, precisely or at least one of $R^1$, $R^2$, $R^3$, and $R^4$ is an R group and/or precisely or at least one of $R^5$, $R^6$, $R^7$, and $R^8$ is an R group. In particular embodiments, $R^3$ or $R^7$ or both are R groups, or $R^2$ or $R^6$ or both are R groups. The one or more R groups may independently contain at least or more than 1, 2, 3, 4, 5, or 6 carbon atoms and up to, for example, 8, 10, 12, 15, 20, 25, or 30 carbon atoms, or any number of carbon atoms within a range bounded by any two of the foregoing values (e.g., 1-30, 1-20, 1-12, 1-8, 1-6, 1-4, 1-3, 6-30, or 12-30 carbon atoms). In particular embodiments, the one or more R groups are linear or branched alkyl groups having any of the carbon numbers or ranges thereof provided above.

In a second set of embodiments, at least one of $R^1$, $R^2$, $R^3$, $R^4$, $R^5$, $R^6$, $R^7$, $R^8$, $R^9$, and $R^{10}$ (or at least one of $R^1$, $R^2$, $R^3$, $R^4$, $R^5$, $R^6$, $R^7$, and $R^8$) is an —OR' group, or at least two, three, or four of $R^1$, $R^2$, $R^3$, $R^4$, $R^5$, $R^6$, $R^7$, $R^8$, $R^9$, and $R^{10}$ (or at least two, three, or four of $R^1$, $R^2$, $R^3$, $R^4$, $R^5$, $R^6$, $R^7$, and $R^8$) are —OR' groups. In the case where R' is a hydrogen (H) atom, one or more —OR' groups are hydroxy (OH) groups; in the case where R' is an R group, one or more —OR' groups are —OR groups. If more than one —OR' group is present, the —OR' groups may be the same or different. In some embodiments, $R^1$, $R^2$, $R^3$, $R^4$, $R^5$, $R^6$, $R^7$, $R^8$, $R^9$, and $R^{10}$ (or $R^1$, $R^2$, $R^3$, $R^4$, $R^5$, $R^6$, $R^7$, and $R^8$) are selected from —OR' groups (or —OH or —OR groups) and hydrogen atoms, and one or more additional groups selected from groups (ii) and (iv)-(vi) may or may not be present. In some embodiments, precisely or at least one of $R^1$, $R^2$, $R^3$, and $R^4$ is an —OR' (or an —OH or —OR) group and/or precisely or at least one of $R^5$, $R^6$, $R^7$, and $R^8$ is an —OR' (or an —OH or —OR) group. In particular embodiments, $R^3$ or $R^7$ or both are —OR' groups (or —OH or —OR groups), or $R^2$ or $R^6$ or both are —OR' groups (or —OH or —OR groups). In the case where one or more —OR groups are present, the one or more —OR groups may independently contain at least or more than 1, 2, 3, 4, 5, or 6 carbon atoms and up to, for example, 8, 10, 12, 15, 20, 25, or 30 carbon atoms, or any number of carbon atoms within a range bounded by any two of the foregoing values (e.g., 1-30, 1-20, 1-12, 1-8, 1-6, 1-4, 1-3, 6-30, or 12-30 carbon atoms). In particular embodiments, the one or more —OR groups are linear or branched alkoxy groups having any of the carbon numbers or ranges thereof provided above. In some embodiments, the R group in an —OR group may (or may not) include a carbonyl (C(O)) group, which may result in an —OC(O)R group. Thus, any of the OR' groups exemplified above may alternatively be an ester group by having a C(O) linkage connect between the oxygen (of the OR' group) and R'. In some embodiments, any one or more of the foregoing —OR' (or —OH or —OR) groups are excluded from the composition.

In a third set of embodiments, at least one of $R^1$, $R^2$, $R^3$, $R^4$, $R^5$, $R^6$, $R^7$, $R^8$, $R^9$, and $R^{10}$ (or at least one of $R^1$, $R^2$, $R^3$, $R^4$, $R^5$, $R^6$, $R^7$, and $R^8$) is an —NR'$_2$ group, or at least two, three, or four of $R^1$, $R^2$, $R^3$, $R^4$, $R^5$, $R^6$, $R^7$, $R^8$, $R^9$, and $R^{10}$ (or at least two, three, or four of $R^1$, $R^2$, $R^3$, $R^4$, $R^5$, $R^6$, $R^7$, and $R^8$) are —NR'$_2$ groups. In some embodiments, both R' groups in the —NR'$_2$ group are hydrogen atoms, which corresponds to a primary amine (—$NH_2$) group. In other embodiments, one R' group in the —NR'$_2$ group is a hydrogen atom and the other is an R group, which corresponds to a secondary amine (—NHR) group. In other embodiments, both R' groups in the —NR'$_2$ group are R groups, which corresponds to a tertiary amine (—$NR_2$) group. One or more of $R^1$-$R^{10}$ (or $R^1$-$R^2$) may be selected from —$NH_2$ groups, —NHR groups, or —$NR_2$ groups. If more than one —NR'$_2$ group is present, the —NR'$_2$ groups may be the same or different. In some embodiments, $R^1$, $R^2$, $R^3$, $R^4$, $R^5$, $R^6$, $R^7$, $R^8$, $R^9$, and $R^{10}$ (or $R^1$, $R^2$, $R^3$, $R^4$, $R^5$, $R^6$, $R^7$, and $R^8$) are selected from —NR'$_2$ groups (or —$NH_2$, —NHR, or —$NR_2$ groups) and hydrogen atoms, and one or more additional groups selected from groups (ii), (iii), (v), and (vi) may or may not be present. In some embodiments, precisely or at least one of $R^1$, $R^2$, $R^3$, and $R^4$ is an —NR'$_2$ (or an —$NH_2$, NHR, or —$NR_2$) group and/or precisely or at least one of $R^5$, $R^6$, $R^7$, and $R^8$ is an —NR'$_2$ (or an —$NH_2$, NHR, or —$NR_2$) group. In particular embodiments, $R^3$ or $R^7$ or both are —NR'$_2$ (or —$NH_2$, NHR, or —$NR_2$) groups, or $R^2$ or $R^6$ or both are —NR'$_2$ (or —$NH_2$, NHR, or —$NR_2$) groups. In the case where one or more NHR or —$NR_2$ groups are present, each R group in the one or more —NHR or —$NR_2$ groups may independently contain at least or more than 1, 2, 3, 4, 5, or 6 carbon atoms and up to, for example, 8, 10, 12, 15, 20, 25, or 30 carbon atoms, or any number of carbon atoms within a range bounded by any two of the foregoing values (e.g., 1-30, 1-20, 1-12, 1-8, 1-6, 1-4, 1-3, 6-30, or 12-30 carbon atoms). In particular embodiments, the one or more R groups in the one or more —NHR or —$NR_2$ groups are linear or branched alkyl groups having any of the carbon numbers or ranges thereof provided above. Notably, in some embodiments, the R group in an —NHR or —$NR_2$ group may (or may not) include a carbonyl (i.e., C(O)) group, which may result in an amide group having the formula —NR'C(O)R or —N(R'C(O)R)$_2$, or in specific embodiments, —NHC(O)R or —NH(C(O)R)$_2$. Thus, any of the amine groups exemplified above may alternatively be an amide group by having a C(O) linkage connect between the nitrogen (of the amine) and R. In some embodiments, any one or more of the foregoing amine or amide groups are excluded from the composition.

In a fifth set of embodiments, at least one of $R^1$, $R^2$, $R^3$, $R^4$, $R^5$, $R^6$, $R^7$, $R^8$, $R^9$, and $R^{10}$ (or at least one of $R^1$, $R^2$, $R^3$, $R^4$, $R^5$, $R^6$, $R^7$, and $R^8$) is a —C(O)R' group, or at least two, three, or four of $R^1$, $R^2$, $R^3$, $R^4$, $R^5$, $R^6$, $R^7$, $R^8$, $R^9$, and $R^{10}$ (or at least two, three, or four of $R^1$, $R^2$, $R^3$, $R^4$, $R^5$, $R^6$, $R^7$, and $R^8$) are —C(O)R' groups. When R' is a hydrogen (H) atom, the —C(O)R' group is an aldehyde (—C(O)H) group; when R' is an R group, the —C(O)R' group is a ketone (—C(O)R) group. If more than one C(O)R' group is present, the R' groups may be the same or different. In some embodiments, $R^1$, $R^2$, $R^3$, $R^4$, $R^5$, $R^6$, $R^7$, $R^8$, $R^9$, and $R^{10}$ (or $R^1$, $R^2$, $R^3$, $R^4$, $R^5$, $R^6$, $R^7$, and $R^8$) are selected from C(O)R' groups and hydrogen atoms, and one or more additional groups selected from groups (ii)-(iv) may or may not be present. In some embodiments, precisely or at least one of $R^1$, $R^2$, $R^3$, and $R^4$ is an C(O)R' group and/or precisely or at least one of $R^5$, $R^6$, $R^7$, and $R^8$ is an C(O)R' group. In particular embodiments, $R^3$ or $R^7$ or both are C(O)R' groups, or $R^2$ or $R^6$ or both are C(O)R' groups.

In the case where one or more —C(O)R groups are present, the one or more R groups may independently contain at least or more than 1, 2, 3, 4, 5, or 6 carbon atoms and up to, for example, 8, 10, 12, 15, 20, 25, or 30 carbon atoms, or any number of carbon atoms within a range bounded by any two of the foregoing values (e.g., 1-30, 1-20, 1-12, 1-8, 1-6, 1-4, 1-3, 6-30, or 12-30 carbon atoms). In particular embodiments, one or more R groups in one or more —C(O)R groups are linear or branched alkyl groups having any of the carbon numbers or ranges thereof provided above. Notably, in some embodiments, the R group in a —C(O)R group may (or may not) include an ether (i.e., —O—) group, which may result in an ester group having the formula —C(O)OR or carboxylic acid group of the formula —C(O)OH. Similarly, in other embodiments, an R group in a —C(O)R group may include an amino linkage (—NH— or —NR—) to result in an amide group, e.g., —C(O)NR'$_2$. Any one or more of $R^1$, $R^2$, $R^3$, $R^4$, $R^5$, $R^6$, $R^7$, $R^8$, $R^9$, and $R^{10}$ (or at least one of $R^1$, $R^2$, $R^3$, $R^4$, $R^5$, $R^6$, $R^7$, and $R^8$) may be any of the foregoing ester or amide groups. In other embodiments, $R^1$, $R^2$, $R^3$, $R^4$, $R^5$, $R^6$, $R^7$, $R^8$, $R^9$, and $R^{10}$ (or $R^1$, $R^2$, $R^3$, $R^4$, $R^5$, $R^6$, $R^7$, and $R^8$) are not permitted to be an ester or amide group. In some embodiments, any one or more of the foregoing carbonyl, ester, or amide groups are excluded from the composition.

In a sixth set of embodiments, at least one of $R^1$, $R^2$, $R^3$, $R^4$, $R^5$, $R^6$, $R^7$, $R^8$, $R^9$, and $R^{10}$ (or at least one of $R^1$, $R^2$, $R^3$, $R^4$, $R^5$, $R^6$, $R^7$, and $R^8$) is a halogen atom, or at least two, three, or four of $R^1$, $R^2$, $R^3$, $R^4$, $R^5$, $R^6$, $R^7$, $R^8$, $R^9$, and $R^{10}$ (or at least two, three, or four of $R^1$, $R^2$, $R^3$, $R^4$, $R^5$, $R^6$, $R^7$, and $R^8$) are halogen atoms. The at least one halogen atom may be selected from fluorine, chlorine, bromine, and iodine atoms. If more than one halogen atom is present, the halogen atoms may be the same or different. In some embodiments, $R^1$, $R^2$, $R^3$, $R^4$, $R^5$, $R^6$, $R^7$, $R^8$, $R^9$, and $R^{10}$ (or $R^1$, $R^2$, $R^3$, $R^4$, $R^5$, $R^6$, $R^7$, and $R^8$) are selected from halogen atoms and hydrogen atoms, and one or more additional groups selected from groups (ii)-(v) may or may not be present. In some embodiments, precisely or at least one of $R^1$, $R^2$, $R^3$, and $R^4$ is a halogen atom and/or precisely or at least one of $R^5$, $R^6$, $R^7$, and $R^8$ is a halogen atom. In particular embodiments, $R^3$ or $R^7$ or both are halogen atoms, or $R^2$ or $R^6$ or both are halogen atoms.

Moreover, although Formula (1) depicts a specific tautomeric arrangement, Formula (1) is intended to include any other tautomers that can be derived from or interconvert with the tautomer shown in Formula (1). As well known, tautomeric structures have the same atomic connections (aside from one or more protons) but differ in the placement of double bonds, generally with concomitant relocation of one or more protons. Moreover, in some embodiments, any one or more groups (ii)-(vi) are excluded from any of the compositions described herein.

In Formula (1), $X^{m-}$ is an anionic species with a magnitude of charge m, where m is an integer of at least 1, provided that n×m=1. The variable n is any number that, when multiplied with m, results in 1. Thus, where the anionic species is a halide (−1 charge, e.g., chloride), n and m are both 1. However, where the anionic species is sulfate (−2 charge), n is 1%2 and m is 2, which indicates more than one extractant compound associated with each sulfate.

In some embodiments, the anionic species ($X^{m-}$) may be any anionic species that, when complexed as a salt with the guanidinium portion shown in Formula (1), can be exchanged for another anionic species desired to be removed from an aqueous solution. As the different anionic species have different dissociation constants, any anionic species may be useful in exchanging with another anionic species to be removed from an aqueous source.

In other embodiments, the anionic species is a species that has been removed from a liquid source, wherein the resulting salt of the complexed anion and oxyanion precipitating compound is valuable as a precursor for generating a free form of the compound of Formula (1) or for recovering a metal present in the oxyanion (e.g., rhenium), or the salt can be used to exchange with another anionic species to remove the other anionic species. The anionic species ($X^{m-}$) can be, for example, a halide, such as fluoride, chloride, bromide, or iodide. The anionic species can alternatively be a halide equivalent (or pseudohalide), such as methanesulfonate (mesylate), trifluoromethanesulfonate (triflate), tosylate, cyanate, thiocyanate, cyanide, or a sulfonamide anion, such as bis(trifluoromethane)sulfonamide (i.e., bistriflimide). The anionic species may alternatively be a borate anion, such as tetrafluoroborate, tetrakis(pentafluorophenyl)borate, or tetrakis[3,5-bis(trifluoromethyl)phenyl]borate. The anionic species may alternatively be hexafluorophosphate ($PF_6^-$). The anionic species may alternatively be hydroxide, or an alkoxide (e.g., methoxide or ethoxide). The anionic species may alternatively be a carboxylate species, such as formate, acetate, propionate, or glycolate. In other embodiments, the anionic species ($X^{m-}$) can be an oxyanion, typically included in the structure by complexation from an aqueous solution.

As used herein, the term "oxyanion" refers to an anion having at least three or four oxygen atoms, wherein the oxygen atoms are generally all bound to a central element. Some examples of oxyanions include sulfate (e.g., $SO_4^{2-}$), nitrate ($NO_3^-$), chromate (e.g., $CrO_4^{2-}$), selenite (e.g.

$SeO_3^{2-}$), selenate (e.g., $SeO_4^{2-}$), tellurate (e.g., $TeO_4^{2-}$, $TeO_{66}$, or $H_5TeO_6$–), arsenite ($AsO_3^{3-}$ or $AsO_2^-$), phosphate (e.g., $PO_4^{3-}$), arsenate ($AsO_4^{3-}$), carbonate ($CO_3^{2-}$), bicarbonate ($HCO_3^-$), and perchlorate ($ClO_4^-$). Some of the oxyanions, such as chromate, are metal oxyanions. Other metal oxyanions include, for example, rhenate, tungstate, vanadate, molybdate, and stannate. The metal in the metal oxyanion is typically a transition metal (e.g., any of Groups 3-12 of the Periodic Table) or a main group metal (e.g., Groups 13, 14, 15, or 16 of the Periodic Table). The oxyanions provided above may or may not also include related derivatives. For example, unless otherwise stated, the term "sulfate" may also include thiosulfate ($S_2O_3^{2-}$), bisulfate ($HSO_4^-$), and sulfite ($SO_3^{2-}$). Similarly, the term "chromate" may also include $Cr_2O_7^{2-}$ (dichromate). Similarly, the term "phosphate" may also include hydrogenphosphate ($HPO_4^{2-}$), dihydrogenphosphate ($H_2PO_4^-$), pyrophosphate ($P_2O_7^{4-}$), thiosphosphates (e.g., $PO_3S^{3-}$ or $PO_2S_2^{3-}$), and phosphite (e.g., $PO_3^{3-}$, $HPO_3^{2-}$, or $H_2PO_3^-$). In some embodiments, the anionic species ($X^{m-}$) is an oxyanion species, such as any of those provided above.

In particular embodiments, at least one of $R^1$, $R^2$, $R^3$, $R^4$, $R^5$, $R^6$, $R^7$, and $R^8$ in the oxyanion precipitating compound is an —OR' group, which may be an —OH or —OR group. In some embodiments, at least two or more of $R^1$, $R^2$, $R^3$, $R^4$, $R^5$, $R^6$, $R^7$, and $R^8$ in the oxyanion precipitating compound are —OR' groups, which may be —OH and/or —OR groups. In some embodiments, precisely or at least one of $R^1$, $R^2$, $R^3$, and $R^4$ is an —OR' (or an —OH or —OR) group and/or precisely or at least one of $R^5$, $R^6$, $R^7$, and $R^8$ is an —OR' (or an —OH or —OR) group. In particular embodiments, $R^3$ or $R^7$ or both are —OR' groups (or —OH or —OR groups), or $R^2$ or $R^6$ or both are —OR' groups (or —OH or —OR groups). In more particular embodiments, the oxyanion precipitating compound has the following structure:

(1a)

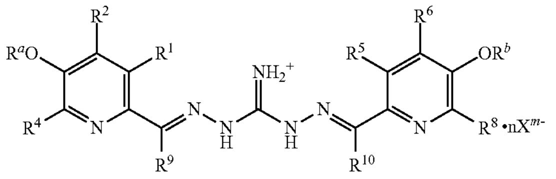

In Formula (1a), $R^1$, $R^2$, $R^4$, $R^5$, $R^6$, $R^8$, $R^9$, and $R^{10}$ the anionic species ($X^{m-}$) are as defined above and may be selected from any of the groups described above, and $R^a$ and $R^b$ are linear or branched alkyl or alkenyl groups containing 1-30 carbon atoms, all of which have been described above. In other embodiments, one or both of —$OR^a$ and —$OR^b$ may be hydroxy (—OH).

The compounds according to Formula (1) can be synthesized by methods well known in the art, as further discussed in the Examples section. For example, to produce compounds according to Formula (1) in which $R^1$-$R^{10}$ are all hydrogen atoms, 2-pyridinecarboxyaldehyde (2-formylpyridine) can be condensed with an N,N-diaminoguanidine salt (e.g., chloride salt) under moderate temperature and other conditions suitable for effecting an amidation condensation. Similarly, to produce compounds according to Formula (1) in which $R^1$-$R^8$ are hydrogen atoms and $R^9$ and $R^{10}$ are alkyl (e.g., methyl) groups, a 2-acylpyridine (e.g., 2-acetylpyridine) can be condensed with an N,N-diaminoguanidine salt. Similarly, to produce compounds according to Formula (1) in which at least one of $R^1$-$R^8$ is an —OR' group, an alkoxy- or hydroxy-substituted 2-formylpyridine or 2-acylpyridine can be condensed with an N,N-diaminoguanidine salt.

In other embodiments, the oxyanion precipitating compound may be a monopyridyl-iminoguanidinium compound having the following structure:

(2)

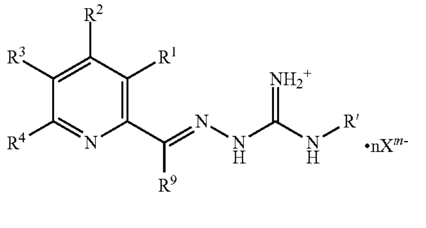

In Formula (2) above, $R^1$, $R^2$, $R^3$, $R^4$, $R^9$ and $X^{m-}$ are as defined under Formula (1) and each may be independently selected from possibilities provided above under Formula (1), including any of the groups (i)-(vi). In some embodiments, $R^1$, $R^2$, $R^3$, $R^4$, and $R^9$ ($R^1$, $R^2$, $R^3$, and $R^4$) are hydrogen atoms. In other embodiments, at least one of $R^1$, $R^2$, $R^3$, $R^4$, and $R^9$ (or at least one of $R^1$, $R^2$, $R^3$, and $R^4$) is not a hydrogen atom, such as wherein at least one of $R^1$, $R^2$, $R^3$, $R^4$, and $R^9$ (or at least one of $R^1$, $R^2$, $R^3$, and $R^4$) is selected from R, —OR', —$NR'_2$, and —C(O)R'. In a first set of embodiments, precisely or at least one or two of $R^1$, $R^2$, $R^3$, $R^4$, and $R^9$ (or precisely or at least one or two of $R^1$, $R^2$, $R^3$, and $R^4$) are selected from R groups, which may be in the presence or absence of one or more other groups (iii)-(vi). In a second set of embodiments, precisely or at least one or two of $R^1$, $R^2$, $R^3$, $R^4$, and $R^9$ (or precisely or at least one or two of $R^1$, $R^2$, $R^3$, and $R^4$) are selected from —OR' groups (i.e., —OH or —OR groups), which may be in the presence or absence of one or more other groups (ii) and (iv)-(vi), and wherein an R group may include a carbonyl linkage to result in an ester group. In a second set of embodiments, precisely or at least one or two of $R^1$, $R^2$, $R^3$, $R^4$, and $R^9$ (or precisely or at least one or two of $R^1$, $R^2$, $R^3$, and $R^4$) are selected from —$NR'_2$ groups (i.e., —$NH_2$, —NHR, or —$NR_2$ groups), which may be in the presence or absence of one or more other groups (ii), (iii), (v), and (vi), and wherein an R group may include a carbonyl linkage to result in an amide group, —NR'C(O)R'. In a third set of embodiments, precisely or at least one or two of $R^1$, $R^2$, $R^3$, $R^4$, and $R^9$ (or precisely or at least one or two of $R^1$, $R^2$, $R^3$, and $R^4$) are selected from —C(O)R' groups (i.e., —C(O)H or —C(O)R groups), which may be in the presence or absence of one or more other groups (ii)-(iv) and (vi), and wherein an R group may include an ether linkage or amino linkage to result in an ester or amide group, e.g., —C(O)OR or —C(O)$NR'_2$. Moreover, in some embodiments, any one or more groups (ii)-(vi) are excluded from any of the compositions described herein.

In another aspect, the invention is directed to a method for removing one or more oxyanions from a liquid source containing the oxyanion by contacting the liquid source with any of the oxyanion precipitating compounds according to Formula (1) or (2) or sub-formula thereof, as described above, wherein the anionic species ($X^{m-}$) in Formula (1), before contact with the liquid source, is exchangeable with the oxyanion to be removed from the liquid source. As a result of the exchange, the resulting salt (i.e., containing the oxyanion precipitating compound complexed with the oxyanion) precipitates from the liquid. In some embodiments, the anionic species in Formula (1), before contact with the liquid source, is more specifically a halide, pseudohalide, or nitrate. The oxyanion(s) in the liquid source can be one or more of any of the oxyanions described above. The oxyanion may be, for example, one or more selected from sulfate, nitrate, selenate, tellurate, phosphate, arsenate, carbonate, bicarbonate, perchlorate, and metal oxyanions (e.g., permanganate, borate, molybdate, vanadate, tungstate, rhenate, chromate, pertechnetate, uranate, thorate, and plutonate). The liquid source may contain any one or more of these oxyanions. In some embodiments, the liquid source contains at least sulfate and/or phosphate, with or without other types of anions or oxyanions being present in the liquid source. In some embodiments, the precipitated salt is separated from the liquid source by means well known in the art, e.g., filtration, decanting, or centrifugation.

The liquid source can be any source (e.g., industrial waste or discharge, agricultural run-off, or seawater) containing one or more oxyanions to be removed. The oxyanion to be removed is generally present in the liquid source as an inorganic salt that is dissolved or suspended in the aqueous source. In some cases, at least one of the oxyanions is in the form of an insoluble scale, which may include one or more of, for example, $CaSO_4$, $SrSO_4$, or $BaSO_4$. Scale is often a significant problem in oil field injection operations and the method described herein offers a solution to scale removal. The oxyanion may also be a metal oxyanion, as often found in effluent from a metal processing or metal mining or nuclear waste operation. The liquid in the liquid source may be an aqueous-based medium (e.g., water or water-solvent mixture) or a non-aqueous medium, such as completely an organic solvent. In some embodiments, the liquid is composed predominantly or completely of water, such as found in seawater, water from sewage treatment, or aqueous effluent from an industrial or commercial process. In other embodiments, the aqueous medium may include an organic solvent miscible in water, such as an alcohol, acetone, or the like.

The anionic species ($X^{m-}$) in the oxyanion precipitating compound of Formula (1), before being contacted with the liquid source, should be capable of being replaced with the oxyanion to be precipitated and removed from the liquid source. Typically, the precipitating compound of Formula (1) or (2) takes the anionic species ($X^{m-}$) as a halide, pseudohalide, or nitrate before contact of the compound of Formula (1) or (2) with the liquid source containing at least one oxyanion, to complex with and precipitate the oxyanion.

Once separated from the liquid source, the precipitated salt may be discarded or incinerated. However, to improve the efficiency and environmental friendliness of the process, the precipitated salt may be subjected to a process that releases the oxyanion and regenerates the uncomplexed precipitating compound. By this process, the oxyanion can be fully separated from the liquid source while making the used precipitating compound available for re-use. More specifically, it has herein been found that the oxyanion precipitating compound can only complex with an oxyanion when the oxyanion precipitating compound is in an open (E,E) form, as depicted in Formulas (1) and (2) and sub-formulas thereof. It has been further found herein that the oxyanion precipitating compound is incapable of complexing with an oxyanion when the oxyanion precipitating compound is in a closed (Z,Z) form. The closed (Z,Z) form is depicted as follows:

(1')

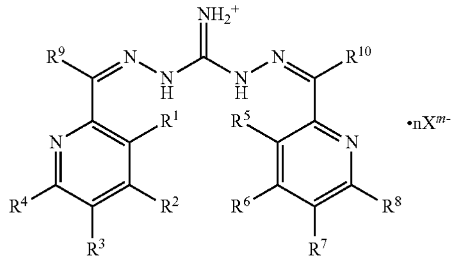

In the above Formula (l'), $R^1$-$R^{10}$ are as defined under Formula (1) or sub-formulas thereof, and $nX^{m-}$ is not an oxyanion (typically, a halide, pseudohalide, or hydroxide).

Of particular importance is the finding herein that the open (E,E) form can be converted to the closed (Z,Z) form of the oxyanion precipitating compound by exposure of the open (E,E) form to electromagnetic radiation, typically having a wavelength in the visible or ultraviolet region, more typically at or below 600 nm (e.g., at or below 550, 500, 450, 400, 350, or 300 nm). Significantly, this photo-switchable property can be exploited to release the precipitating oxyanion in a separate location from the liquid source and also simultaneously regenerate uncomplexed precipitating compound in the process, which can be separated from released oxyanion and re-used to complex with additional oxyanion.

Notably, once uncomplexed closed (Z,Z) precipitating compound is produced, it can be reconverted to the open (E,E) form in solution by exposure to thermal energy, typically a temperature between room temperature (~20 or 25° C.) and 40, 45, or 50° C., typically over a number of hours (e.g., at least 1, 2, 3, 4, 5, or 6 hours). The regenerated open form can then advantageously be re-used for complexation and precipitation of additional oxyanion, and notably, without the use of chemical means for release of the oxyanion and regeneration of the precipitating compound.

In some embodiments, following precipitation of the salt, the salt is removed from the liquid source, transferred to a second liquid, and the salt is exposed to electromagnetic (EM) radiation in the second liquid to isomerize the compound of Formula (1) to the closed (Z,Z) form. Upon exposure to the EM radiation, the oxyanion is released in the second liquid along with production of the uncomplexed closed (Z,Z) form of the precipitating compound. In some embodiments, the second liquid is sufficiently non-polar to make uncomplexed (free) oxyanion precipitate while uncomplexed precipitating compound is substantially soluble in the second liquid. In this way, the oxyanion can be separated from the precipitating compound (e.g., by filtration) in order for the precipitating compound to be re-used.

In further embodiments, the second liquid (e.g., after exposure to electromagnetic radiation) may be contacted with a third liquid substantially insoluble with the second liquid, wherein the uncomplexed precipitating compound is substantially soluble in the third solvent but not the second solvent, and the uncomplexed (free) oxyanion is not soluble in the third solvent and may or may be soluble in the second solvent. The uncomplexed oxyanion may dissolve or precipitate in the second solvent, but not enter the third solvent. In some embodiments, the precipitating compound contains one or more groups (e.g., one or more of $R^1$-$R^{10}$) which confer a hydrophobic property to the precipitating compound (e.g., by containing at least 4, 5, or 6 carbon atoms), and the third solvent is sufficiently hydrophobic (e.g., hexane, toluene, or a halohydrocarbon, such as methylene chloride or chloroform) to substantially dissolve the uncomplexed form of the precipitating compound while not dissolving the free oxyanion; and the second solvent (in contact with but immiscible with the third solvent) is sufficiently polar to retain free oxyanion but substantially incapable of dissolving the uncomplexed form of the precipitating compound. This results in partitioning of the uncomplexed form of the closed oxyanion precipitating compound according to Formula (1') into the third liquid which is in contact with the second liquid. The hydrophobic solution containing the third solvent and uncomplexed precipitating compound can be separated from the second solvent by standard methods, and the third solvent removed to isolate the uncomplexed precipitating compound. The uncomplexed precipitating compound can be thermally converted back to the open (E,E) form before or after separation from the third solvent. In this way, the uncomplexed precipitating compound can be freed and separated from the oxyanion and then re-used for complexation and precipitation of additional oxyanion.

The foregoing described process amounts to an efficient oxyanion removal process whereby one or more oxyanions in a liquid source is/are complexed and precipitated, in some cases selectively. For example, in some embodiments wherein at least two types of oxyanions are present in the liquid, the process described above may result in a yield of at least or greater than 90% or 95% yield of precipitated (removed) oxyanion, wherein the removed oxyanion may have a purity of at least or greater than 85%, 90%, or 95%.

In some embodiments, the oxyanion precipitating compound forms aggregates (e.g., micelles, vesicles, or the like) in the liquid, which can aid in the removal of one or more oxyanions in the liquid. These aggregated species may bind selectively to an oxyanion (e.g., sulfate) and can be retained by filtration whereby other anions pass through the filter, thus resulting in an effective selective filtration. The oxyanion precipitating compound can form aggregated species particularly in the case where one or more R groups in Formula (1) independently contain at least or more than 1, 2, 3, 4, 5, or 6 carbon atoms and up to, for example, 8, 10, 12, 15, 20, 25, or 30 carbon atoms, or any number of carbon atoms within a range bounded by any two of the foregoing values. The aggregated structures can range from spherical, cylindrical, bilayer, or lamellar motifs that can be separated by methods such as ultrafiltration, solvent extraction, centrifugation, and size exclusion chromatography. The aggregated structures contain a multiplicity of the precipitating compounds, e.g., at least or more than 2, 3, 4, 5, 10, 15, or 20 precipitating compounds, associated with one or more oxyanions.

Examples have been set forth below for the purpose of illustration and to describe certain specific embodiments of the invention. However, the scope of this invention is not to be in any way limited by the examples set forth herein.

EXAMPLES

Synthesis of bis(2-((E)-pyridin-2-ylmethylene)hydrazinyl)methaniminium chloride (2PyDIG·HCl)

2PyDIG·HCl was synthesized via previously described methods (R. J. Abraham et al., *J. Med. Chem.*, 59(5), 2126-2138, 2016). Briefly, the condensation between 2-pyridinecarboxyaldehyde (4.40 mmol, 420 μL) and N,N'-diaminoguanidine hydrochloride (2.05 mmol, 257 mg) was performed in a 500 mL vessel in 10 mL ethanol. The reaction mixture was heated to 70° C., left to react for 24 hours, then cooled to room temperature. Diethyl ether was added (5 mL) and the flask was chilled to induce crystallization. The yellow precipitate was filtered and washed three times with 5 mL cold diethyl ether. The product was obtained as a yellow solid (459 mg, 74% yield). $^1$H NMR (400 MHz, DMSO-$d_6$) δ12.31 (s, 2H) 8.75 (s, 1H), 8.67-8.66 (d, J=4.8 Hz, 2H), 8.48 (s, 2H), 8.41-8.39 (d, J=8.0 Hz, 2H), 8.01-7.97 (t, J=7.7 Hz, 2H), 7.53-7.50 (t, J=12.4 Hz, 2H). $^{13}$C NMR (100 MHz, DMSO-$d_6$) δ 152.1, 149.7, 147.7, 145.5, 137.7, 125.5, 121.9; HRMS (ES+) m/z: [M+H$^+$] calcd. 268.1311, found 268.1305. Elemental analysis: calcd. (found) for 2PyDIG·HCl-3$H_2O$: C, 43.64 (44.14), H, 5.63 (5.35), N, 27.40 (27.42).

Synthesis of bis(2-((E)-pyridin-2-ylmethylene)hydrazineyl)methaniminium trifluoromethanesulfonate (2PyDIG·HOTf)

PyDIG·HCl (0.336 mmol, 102 mg) was dissolved in DI water (5 mL) and a solution of silver trifluoromethanesulfonate (0.341 mmol, 87.5 mg) in water (5 mL) was added dropwise. Upon addition, a yellow precipitate immediately formed. After 1 h of stirring, the reaction mixture was filtered, and the yellow solid was washed three times with 10 mL DI water. The aqueous solution of 2PyDIG·HOTf was evaporated under vacuum to produce a yellow solid (109 mg, 77% yield). $^1$H NMR (400 MHz, DMSO-$d_6$) δ 12.29 (s, 2H), 8.75 (s, 1H), 8.70-8.68 (d, J=4.9 Hz, 2H), 8.4 (s, 2H), 8.40-8.38 (d, J=7.9 Hz, 2H), 8.01-7.98 (t, J=7.5 Hz, 2H), 7.53-7.50 (t, J=11.7 Hz, 2H). $^{13}$C NMR (100 MHz, DMSO-$d_6$) δ 153.6, 150.3, 147.6, 146.7, 139.6, 125.7, 122.5, 119.1; HRMS (ES+) m/z: [M+H$^{30}$] calcd. 268.1311, found 268.1304. Elemental analysis: calcd., (found) for 2PyDIG·HOTf-2$H_2O$: C, 37.09 (36.66), H, 4.00 (3.90), N, 21.62 (21.79).

Synthesis of (E)-N—((E)-pyridin-2-ylmethylene)-2-(pyridin-2-ylmethylene)-hydrazine-1-carboximidhydrazide (2PyDIG)

2PyDIG·HCl (0.86 mmol, 262 mg) was dissolved in DI water (5 mL). To the yellow solution, 1 M sodium hydroxide (0.86 mmol, 862 μL) was added dropwise to produce a yellow precipitate. The yellow solid was filtered and washed three times with 5 mL cold DI water. The product was obtained as a yellow solid (232 mg, 89% yield). $^1$H NMR (400 MHz, DMSO-$d_6$) δ 11.36 (s), 8.60-8.54 (d, J=4.5, 2H), 8.33-8.26 (d, J=8.0 Hz, 2H), 8.19 (s, 2H) 7.89-7.80 (t, J=7.2 Hz, 2H), 7.46 (bs) 7.40-7.33 (t, J=11.9 Hz, 2H). $^{13}$C NMR (100 MHz, DMSO-$d_6$) δ 158.1, 154.4, 149.2, 144.2, 136.4, 123.3, 120.1.

Photoirradiation Studies

In a typical photoirradiation NMR experiment, 3 mL of a freshly made deuterated DMSO solution was placed in a quartz cuvette (1 cm×1 cm×4.5 cm), stirred, and irradiated with UV-visible light using an unfiltered super high-pressure mercury lamp with emissions in the long-wave UV region and in the visible region at the yellow, green, blue, and violet wavelengths (254-800 nm). From the irradiated solution, 500 μL aliquots were removed with a micropipette and transferred to NMR tubes. For studies including excess triflate, a stock solution (200 mM) of tetramethylammonium triflate in DMSO-$d_6$ was added before irradiation to obtain the desired concentration. Experiments were carried out in the same fashion as above. All measurements were obtained on the irradiated solutions within 1 hour of irradiation. $^1H$ spectra were recorded on a Bruker AvanceIII-400 MHz NMR spectrometer equipped with a 5 mm PABBO probe. The residual solvent signal ($(CD_3)_2SO$ δH=2.50 ppm) was considered as an internal reference to calibrate spectra and the temperature was held at 24° C. The chemical shifts used to monitor photoisomerization were the set of doublets at 8.67 and 8.80 ppm and triplets at 7.54 and 7.68 ppm for the E,E and Z,Z isomers, respectively. To rule out the possibility of sub-millimolar concentrations of unconverted E,E isomer undetectable by NMR, a $^1H$ NMR spectrum was collected with a very long acquisition time (ns=512), which showed good signal-to-noise ratio but no trace of the E,E isomer. The sample underwent hydrolysis back to the aldehyde only under forcing conditions of heating the sample at 50° C. for 2 weeks in water, where the aldehyde proton at 9.86 ppm started to resolve.

A hypothesis test was performed using a p-test to declare that there is sufficient evidence to infer that there is no evidence of a difference between observed and noise chemical shifts in the $^1H$ NMR chemical shift. P-values for the open E,E form chemical shifts was $3.3 \cdot 10^{-12}$, while the closed Z,Z form was 0.208. A $\chi^2$ value was also used to check the goodness of fit for the data, in which case both sets of data were below the critical value.

Cycling studies were performed by irradiating a freshly prepared, 9.94 mM 2PyDIG·HOTf DMSO-$d_6$ solution in an NMR tube at 24° C. After 6 hour, a $^1H$ NMR spectrum was collected to determine the photoisomerization value, and the sealed NMR tube was placed in a 50° C. oven. The sample was heated statically for 24 hour, at which point the solution was left to cool at room temperature for approximately 30 min, and a $^1H$ NMR spectrum was collected to determine the thermal relaxation value. This cycling process was repeated three more times.

Photoswitching in the presence of sulfate was performed in one of two methods. In the first method, 0.5 mol ratio (sulfate to $2PyDIG^+$) tetramethylammonium sulfate was added to a freshly prepared 10 mM E,E-2PyDIG·HOTf in DMSO-$d_6$ solution in a quartz cuvette. After the addition of sulfate, the solution was irradiated with a UV (Hg lamp) light for 2 hours while stirring. The solution was then heated statically for 36 hours, at which point the solution was left to cool at room temperature for approximately 30 minutes, and a $^1H$ NMR spectrum was collected. In the second method, a freshly prepared 10 mM E,E-2PyDIG·HOTf in DMSO-$d_6$ solution was irradiated with UV (Hg lamp) light for 2 hours while stirring. Following this, tetramethylammonium sulfate was added in either 0.5 or 1.0 mol ratio (sulfate to $2PyDIG^+$). The solution was then heated statically for 36 hours, at which point the solution was left to cool at room temperature for approximately 30 minutes, and a $^1H$ NMR spectrum was collected. $^1H$ NMR spectra were collected on 500 μL aliquots of the freshly prepared samples, samples after photoirradiation, and samples after thermal treatment at 50° C. for 36 hours.

X-Ray Crystallography

Single crystals of E,E-$2PyDIG_2 \cdot H_2SO_4$ were obtained by in-situ synthesis and crystallization. N,N'-diaminoguanidine hydrochloride (0.192 mmol, 24 mg) and tetramethylammonium sulfate (0.094 mmol, 23 mg) were added to 20 mL ethanol and the mixture was shaken. To the clear, colorless solution, 2-pyridinecarboxaldehyde (0.393 mmol, 37 μL) was added. After 3 weeks at room temperature, clear, pale yellow blade-like crystals were obtained from the clear, yellow mother liquor.

Single crystals of Z,Z-2PyDIG $HBPh_4$ were obtained by irradiating a ca. 1.5 mM solution of 2PyDIG HCl in methanol for 1 hour. After irradiation, the solution was used to dissolve sodium tetraphenylborate (0.004 mmol, 1.2 mg) with mild shaking. The clear, faint yellow solution was left for 5 days, at which point faint yellow blade-like crystals were obtained.

Diffraction data were collected at 100 K on a diffractometer with graphite monochromator using Mo Kα radiation (λ=0.71073 Å). The frames were integrated with a commercial software package using a narrow-frame algorithm. An empirical absorption correction using the Multi-Scan method SADABS was applied to the data. The structure was solved by direct methods using a commercial software package.

Titration Studies

For absorption titration experiments, a freshly prepared stock solution of 1.5 mM E,E-2PyDIG·HOTf in DMSO-$d_6$ was added to a 1 mm quartz cuvette, and a tetramethylammonium sulfate solution (3.6 mM in DMSO-$d_6$) was added, and the solution was mixed. Absorption spectra were collected after each addition using a UV-Visible spectrophotometer at ca. 24° C. For the Z,Z photoisomer, a freshly prepared 1.5 mM 2PyDIG·HOTf sample was irradiated for 1 hour before titration experiments were prepared and carried out in the same manner as for the E,E isomer.

The binding constants from the three UV-Vis titrations were calculated using commercial software based on the changes in the $2PyDIG^+$ absorption maximum value at 315 nm and 320 nm for the E,E and Z,Z photoisomers, respectively. Fitting was performed by assigning the 1:0 and 1:2 PyDIG:sulfate adducts as spectra from before addition of sulfate and after 3 molar equivalents of sulfate, respectively.

All titration trials show the same behavior upon addition of sulfate. Initially, for the E,E isomer, the monoprotonated 2PyDIG cation binds to the titrated sulfate ion, forming the dominant $[(2PyDIG)_2(SO_4)]$ species in solution at 0.5 equivalents sulfate added. Upon further sulfate titration, the 1:1 form, $[(2PyDIG)(SO_4)]$-, forms at 1.0 equivalents added. The 1:2 species, $[(2PyDIG)(SO_4)_2]$, is the predominant form after 2.0 equivalents of titrated sulfate are added. For the Z,Z isomer a three species fitting was employed, with no dominant species forming.

For $^1H$ NMR titrations, a freshly prepared stock solution of 1.5 mM 2PyDIG·HOTf in DMSO-$d_6$ was added to twelve NMR tubes, and a tetramethylammonium sulfate solution (10 mM in DMSO-$d_6$) was added in varying stoichiometric amounts. Clean DMSO-$d_6$ was then added to achieve a final volume of 500 μL. Titrations were performed with both a micropipette and a micrometer syringe. For the Z,Z photoisomer, a freshly prepared 1.5 mM 2PyDIG·HOTf sample was irradiated for 1 hour before the six titration experiments were prepared and carried out in the same manner as for the E,E isomer. To ensure that the PyDIG concentration was not changing as a result of precipitation, dimethylsulfone was added as an internal standard to the 1:2 PyDIG:$SO_4$ solution. It was determined that the concentration of PyDIG remained constant throughout the experiment.

The binding constants from the four $^1H$ NMR titrations were calculated using commercial software based on the changes in the guanidinium —N—H chemical shifts of the 2PyDIG protons. During fitting, only the monoprotonated 2PyDIG cation was considered, as the Bjerrum pair of 2PyDIG cation and triflate in DMSO was estimated to have a $K_{association}$ value of 156 $M-^1$. Fitting was performed by locking the 1:0 and 1:2 PyDIG:sulfate adducts at known chemical shift values to reduce the number of adjustable parameters to refine. The corresponding speciation and residual plots for each trial made. Attempts to increase the experimental concentration of 2PyDIG·HOTf higher than 1 mM produced solids, which prevented NMR titrations at higher concentrations.

Photoswitching Mechanism

Photoswitching between the open E,E and closed Z,Z photoisomers provides a binding-release mechanism for efficient oxyanion separations. The photoswitching binding-release mechanism is schematically depicted in FIG. 1. The present work describes the first example of photoisomerization using an iminoguanidinium cation, as specifically demonstrated using 2-pyridyl-diiminoguanidinium (2PyDIG) and corresponding photoswitched binding of the model oxyanion sulfate. This receptor is easily prepared in one step by condensation of 2-pyridinecarboxaldehyde with N,N-diaminoguanidine hydrochloride. Photoisomerization in DMSO-$d_6$ with UV light was monitored through $^1$H NMR and UV-vis spectroscopies, supported by density functional theory (DFT) electronic-structure calculations and X-ray crystal structures of both the sulfate-bound E,E form and the nonbinding Z,Z photoisomer. Upon photoconversion, the binding of sulfate is essentially shut off in the Z,Z form, resulting in a five-orders-of-magnitude light-induced reversible switching of anion-binding strength, as determined by UV-absorption and $^1$H NMR titrations, which may be among the largest photoinduced change in anion-binding strength yet reported.

Figure 2:
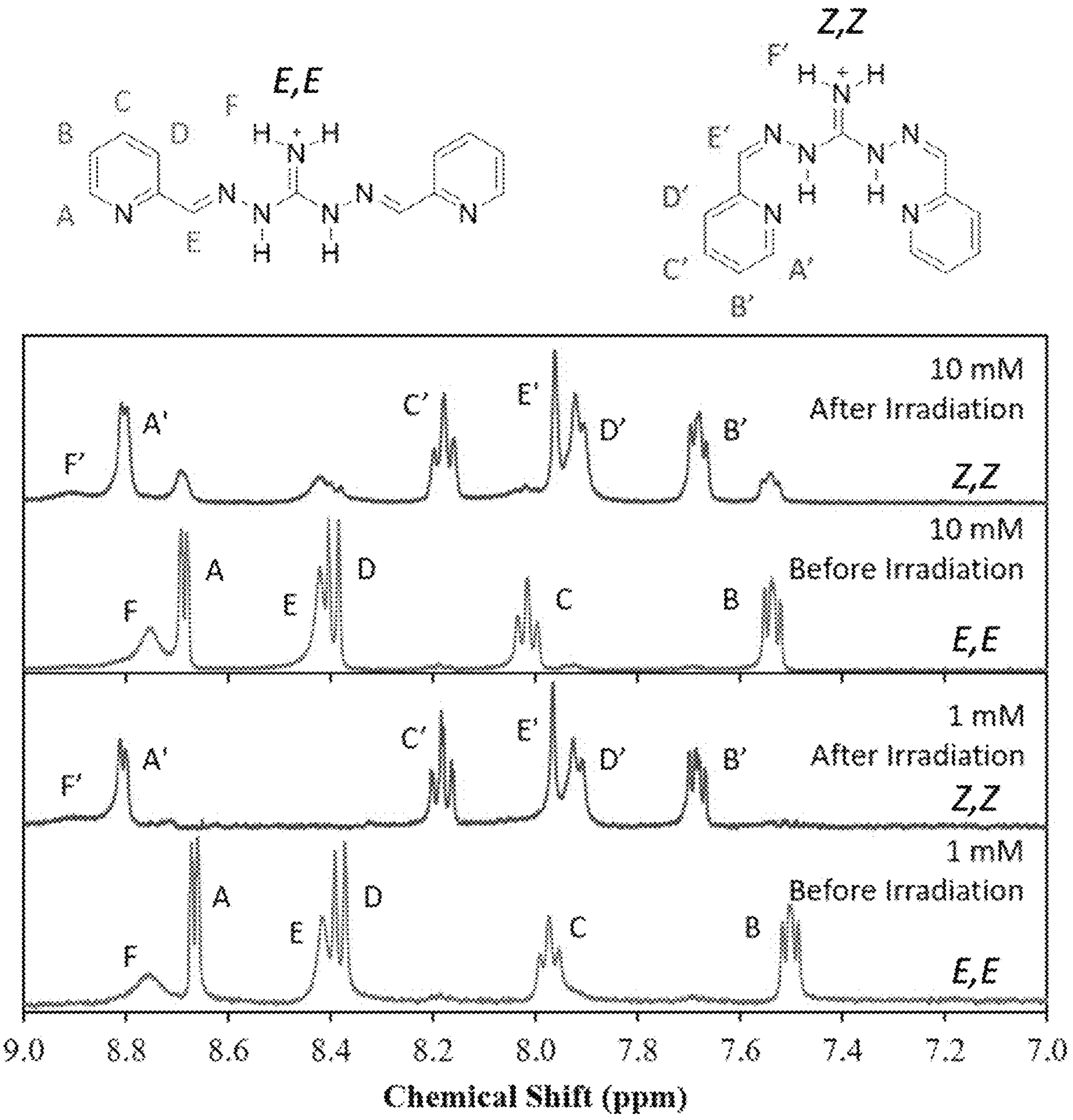
FIG. 2. Top: E,E and Z,Z structures (left and right, respectively) of the 2PyDIG precipitating compound. Bottom: $^1H$ NMR (400 MHz) spectra of the aromatic region for 1.01 mM (bottom two spectra) and 10.03 mM (top two spectra) 2PyDIG·HOTf in DMSO-$d_6$ at 24° C. before (blue) and after (red) 1 hour UV photoirradiation.

Photoisomerization and Thermal Relaxation Behavior $^1$H NMR spectroscopy confirmed the photoconversion of the open E,E to the closed Z,Z form of 2PyDIG. The structures of the E,E and Z,Z forms of 2PyDIG are shown at the top of FIG. 2. The 2PyDIG receptor was initially prepared as the chloride salt, followed by an exchange to the triflate ($TfO^-$) salt, where triflate was expected to be much less competitive in anion-binding studies. To probe the ability of 2PyDIG to photoisomerize in the presence of UV light, its triflate salt in DMSO-$d_6$ (ca. 1 mM and 10 mM concentrations) was photoirradiated with an unfiltered Hg vapor lamp for 6 hours. The $^1$H NMR spectrum of the open E,E-2PyDIG·HOTf (FIG. 2, bottom) at 1 mM in DMSO-$d_6$ consists of only seven peaks, consistent with its symmetry: four peaks at $\delta$=8.67, 8.39 ppm as doublets and 7.98 and 7.54 ppm as triplets corresponding to pyridine protons, a broad singlet at 8.74 ppm corresponding to the guanidinium protons ($=NH_2$), a slightly broad overlapping singlet at 8.42 ppm from the imine proton (—N=CH), and lastly, the most downfield resonance at 12.21 ppm (not shown in FIG. 2) is assigned to the guanidinium —N—H protons. After UV irradiation (Hg vapor lamp), the photoconverted Z,Z photoisomer also gives rise to seven unique resonances different from those of the E,E form, initially with no observable E,E isomer present above experimental noise in the case of the 1 mM solution. Resonances corresponding to pyridine proton signals at 8.18 and 7.68 ppm appear as triplets, while a set of doublets, one at 8.80 ppm and the second at 7.91 ppm overlap with the sharp singlet corresponding to the imine proton at 7.96 ppm. The guanidine N—H proton resonance shifts downfield from 12.21 in the E,E isomer to 15.05 ppm after photoirradiation to the Z,Z form. This significant downfield shift is indicative of a drastic change in environment around the proton, consistent with the presence of intramolecular hydrogen bonding. The chemical shifts of the non-exchangeable protons of two forms align closely with DFT-generated $^1$H NMR spectra, except for the imine protons, which are systematically shifted to higher field. While different populations of rotational isomers are expected based on DFT calculations, the simplicity of the NMR spectra suggests a fast exchange about the C—N bonds at room temperature for both the E,E and Z,Z forms. Lastly, no evidence of the intermediate E,Z isomer could be detected in the NMR spectra, pointing to its transient nature under these conditions.

Figure 3:
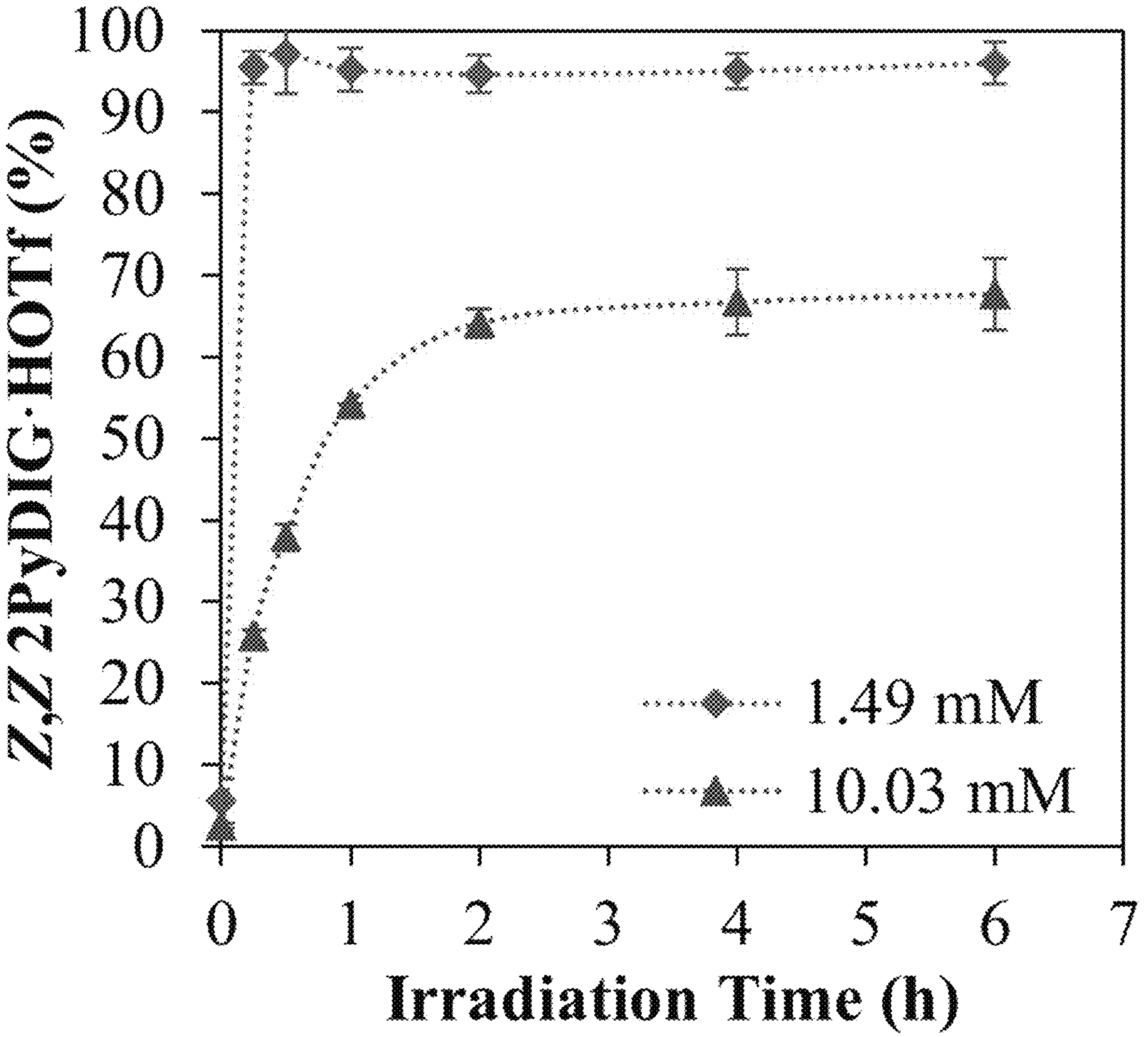
FIG. 3. Graph showing conversion of 1.49 mM (blue) and 10.03 mM (red) E,E 2PyDIG·HOTf to the Z,Z photoisomer over the course of 6 hours at 24° C. under UV irradiation in DMSO-$d_6$. Dotted lines are for visual aid.

Stirred solutions of 1.5 and 10 mM 2PyDIG exposed to UV light reach photostationary states (FIG. 3), as indicated by the evolution of their $^1$H NMR spectra monitored at various time intervals. Thus, irradiation of freshly prepared samples causes a progressive disappearance of the E,E isomer signals, while a new set of signals from the Z,Z isomer grows in. At 1.5 mM, the E,E isomer (with initially 5.5±0.5% Z,Z isomer), reaches 95.6±0.4% photoconversion to the Z,Z isomer in less than 15 min; at the 95% confidence level, this is indistinguishable from complete conversion. Visual inspection of the chemical-shift region 8.35-8.70 ppm shows no apparent trace of the E,E isomer remaining. In the 10 mM solution, however, it takes a little more than 2 hours to reach a PSS consisting of 67.7±4.4% Z,Z isomer. Thus, while under conditions of low concentration the degree of conversion at PSS is exceptional for a photoswitched anion receptor, more typical behavior is obtained at higher concentrations.

Figure 4:
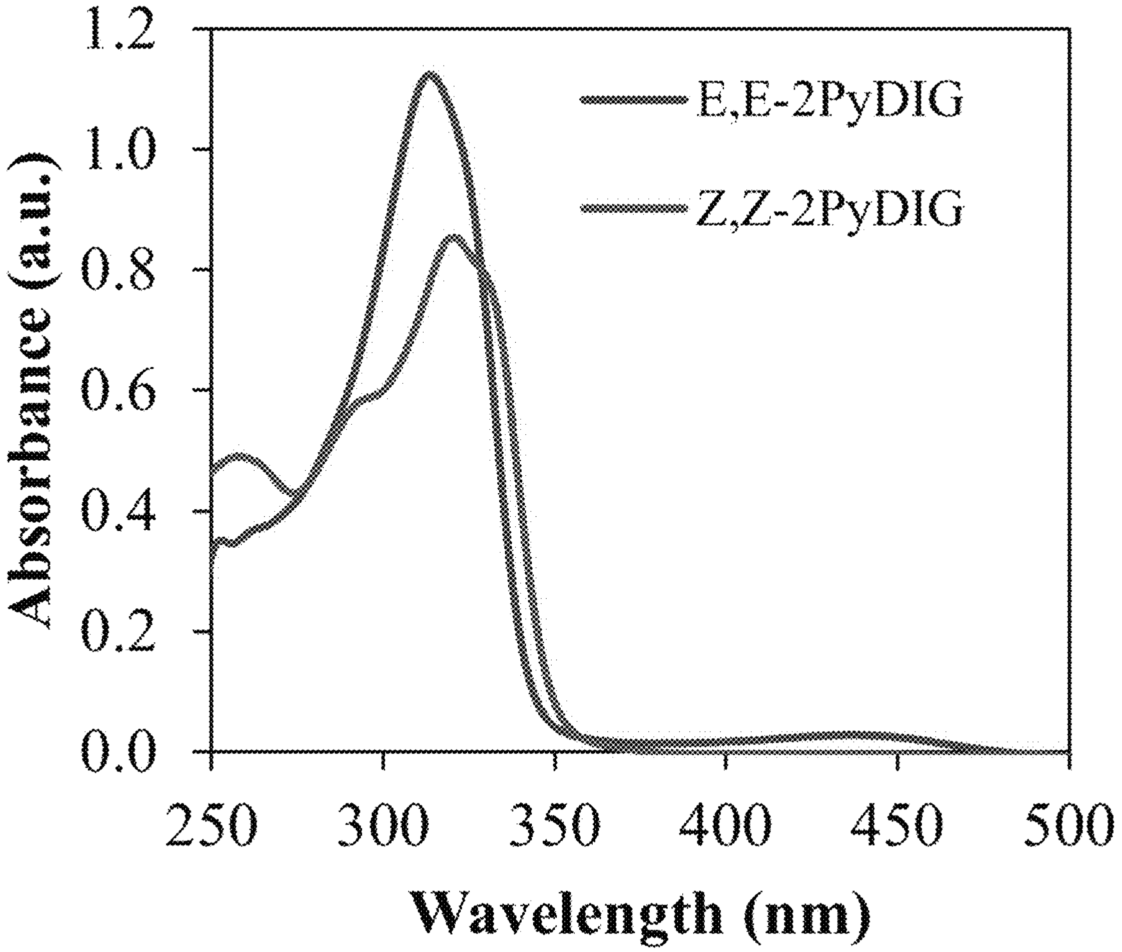
FIG. 4. Absorption spectrum of 1.21 mM E,E-($\lambda_{max}$=315 nm) and Z,Z-2PyDIG·HOTf ($\lambda_{max}$=320 nm) in DMSO-$d_6$.

The absorption maximum of the 2PyDIG cation in its near-UV spectrum undergoes a slight bathochromic shift from 315 nm to 320 nm during UV irradiation as a result of E,E to Z,Z conversion, as depicted in FIG. 4. The absorption spectrum of 2PyDIG·HOTf in DMSO-$d_6$ contains features between 260-350 nm, which are attributed mainly to allowed $\pi$-$\pi^*$ transitions that dominate much weaker n-$\pi^*$ transitions involving pyridine lone pairs, while the transition involving the lone pairs of the C=N groups occur at higher energies. Shoulders below 285 nm as well as the main absorption bands in the range 310-350 nm correspond to the $\pi$-$\pi^*$ transitions of the extended conjugated systems involving both the iminoguanidinium moiety and the pyridyl rings. The transition at 440 nm is tentatively assigned to aggregates of the 2PyDIG receptors in solution, as this peak disappears upon dilution. The minor bathochromic shift upon photoisomerization from the E,E to Z,Z has been previously reported in acylhydrazone systems, as both isomers retain their planarity (D. J. van Dijken et al., *J. Am. Chem. Soc.*, 137 (47), 14982-14991, 2015).

Figure 5:
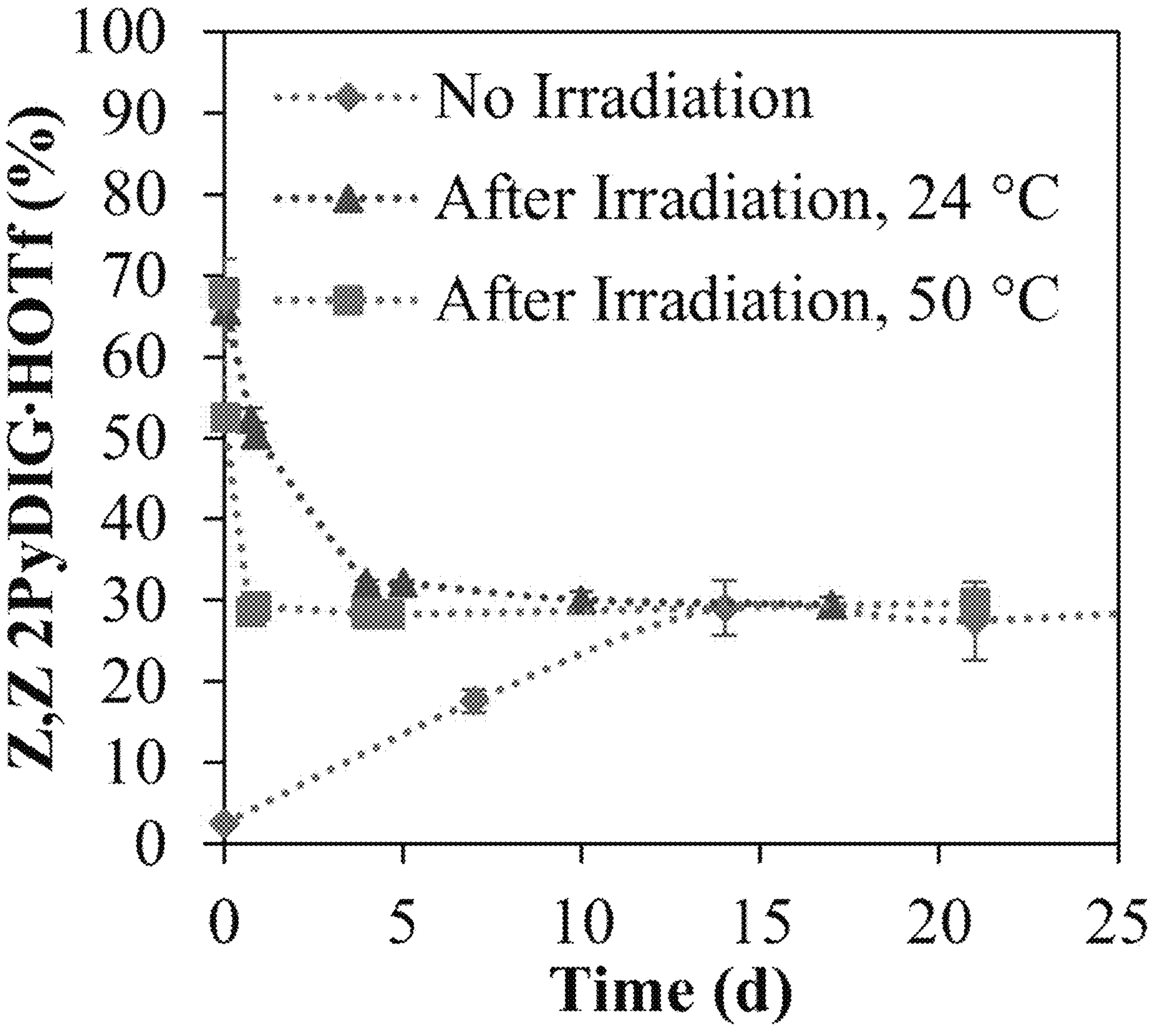
FIG. 5. Thermal relaxation of 10.03 mM 2PyDIG/HOTf in DMSO-$d_6$ after irradiation, at 24° C. (red) and 50° C. (green), and the non-irradiated E,E isomer at 24° C. (blue) converging at a thermal equilibrium. Dotted lines are for visual aid.

Both photoirradiated and freshly prepared (nonirradiated) 2PyDIG HOTf solutions behave as T-type photoswitches, thermally relaxing to a common thermal equilibrium of 70.5±0.9% E,E isomer. Thermal relaxation was investigated by monitoring the photoirradiated solutions at 24° C. and 50° C. (FIG. 5). At 10 mM, thermal equilibrium is reached after 4 d at 24° C., and less than 24 h at 50° C. Unirradiated E,E isomer thermally equilibrates to the same state in 14 d at 24° C. These results indicate two underlying processes that lead to a common equilibrium point: the spontaneous conversion from EE to ZZ under normal visible light, and the back reaction from ZZ to EE under normal visible light and thermal heating. The thermal relaxation equilibrium back to E,E from Z,Z corresponding to Eq. 1 has an implied equilibrium constant of 2.38(8) that is independent of temperature, suggesting an enthalpy and entropy change close to zero.

$$(E, E)^+ \underset{K_{relax}=2.4}{\overset{hv}{\rightleftharpoons}} (Z, Z)^+ \qquad (1)$$

An intramolecular imine-enamine tautomerization that lowers the energy barrier between Z to E isomers through an inversion mechanism has been hypothesized (e.g., S. Ludwanowski et al., *Chem. Eur. J.,* 26 (58), 13203-13212, 2020). In the present system, the reversion from the Z,Z to E,E isomer at 24° C. appears to follow a second-order process, which implies a bimolecular isomerization mechanism possibly facilitated by intermolecular proton transfer. The concentration-dependence of the reversion rate may explain in part the decrease in the degree of conversion to the Z,Z isomer at PSS at 10 mM 2PyDIG shown in FIG. 3. Efforts to understand both the forward and reverse processes in more detail are currently underway. Interestingly, the thermal relaxation behavior (both rate and end state) does not change upon the addition of 10 or 50 mM excess triflate, which indicates this anion acts as a spectator and does not facilitate the reversion. However, the presence of sulfate drives the reversion to near completion (vide infra). Finally, photoirradiation and thermal relaxation of a 10 mM 2PyDIG solution can be cycled several times in DMSO without signs of fatigue. Cycles consisted of 6-hour irradiation times followed by 24-hour dark equilibrations, the percent Z,Z isomer switching between values of 69% and 25%, respectively. Cycling experiments at lower concentrations were not practical since the time required for a 1 mM 2PyDIG solution to reach thermal equilibrium, even at elevated temperatures, is greater than 20 days.

X-Ray Crystal Structure Analyses of E,E and Z,Z 2PyDIG Photoisomers

Figure 6:
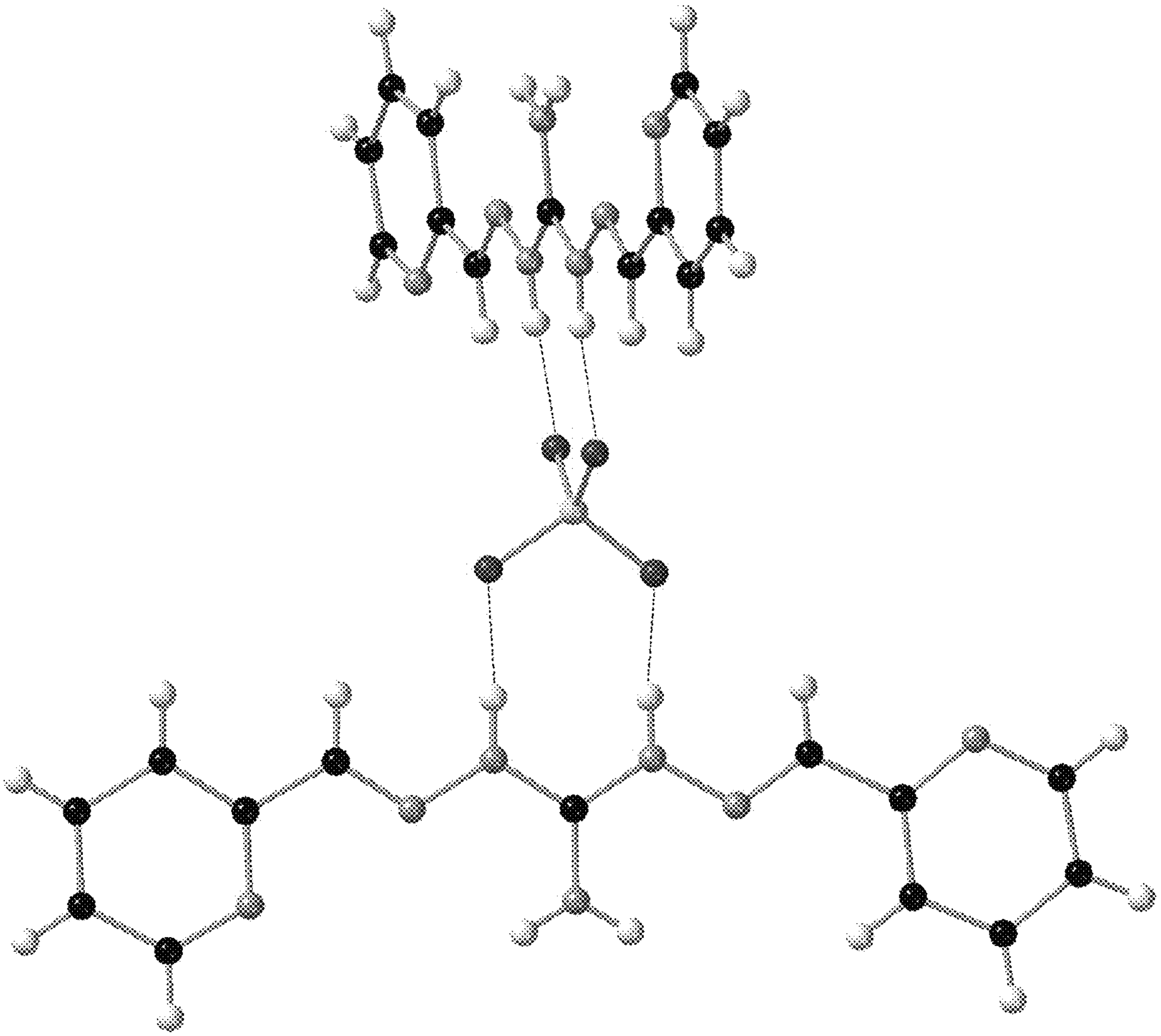
FIG. 6. Crystal structure of E,E-$2PyDIG_2 \cdot H_2SO_4$ highlighting the 2:1 sulfate binding by the 2PyDIG cations. Yellow spheres are sulfur atoms, red spheres are oxygen atoms, blue spheres are nitrogen atoms, black spheres are carbon atoms, and white spheres are hydrogen atoms. Solvent molecules have been removed for clarity. Hydrogen bonds to sulfate are depicted as dotted lines.

The crystal structure of the open E,E-2PyDIG receptor, as sulfate salt, highlights the characteristic bidentate N—H hydrogen-bonding from two guanidinium cations along opposite O—S—O edges of sulfate. As depicted in FIG. 6, the 2PyDIG cation is planar, with a dihedral angle of 177.7° between carbon atoms of the two pyridine rings. A 2:1 guanidinium:sulfate binding is found in the crystal, with the two 2PyDIG cations nearly orthogonal to each other (104.50), and with measured N—H . . . O contact distances varying between 1.82 and 1.84 Å. The crystal packing involves mainly N—H . . . O hydrogen bonds between the —$NH_2$ guanidium protons and solvent molecules, combined with stabilizing π-πinteractions, with distances between pyridine rings of 4.38 Å and a slippage angle of 49.14°. A similar structural motif has been reported for sulfate binding by N,N-bis(2-pyridyl)guanidinium, sharing the dual hydrogen bonding to opposite O—S—O edges and stabilizing intramolecular hydrogen bonding of the guanidine —$NH_2$ group to the pyridines (C. A. Seipp et al., *RSC Adv.,* 5(130), 107266-107269, 2015).

Figure 7:
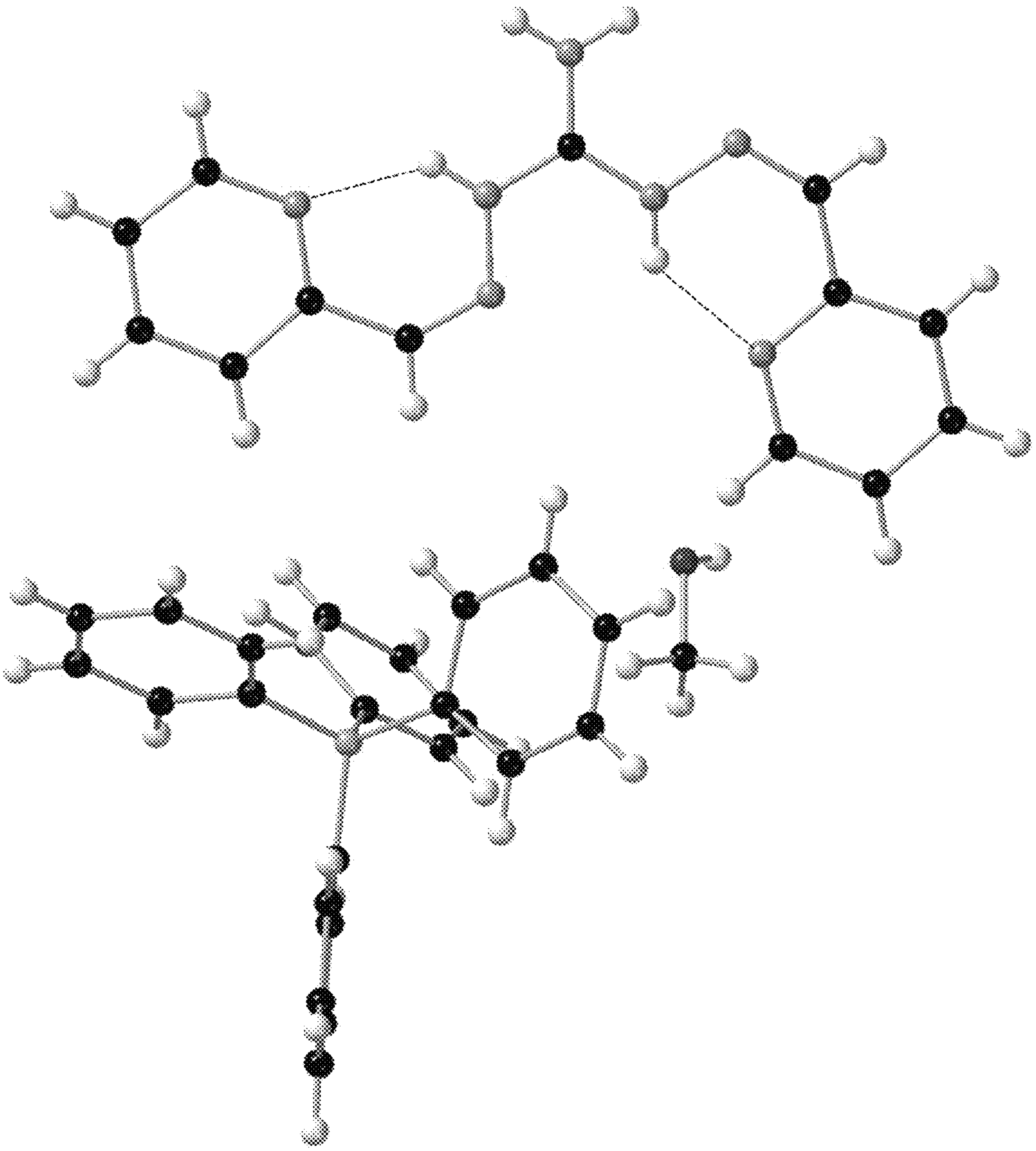
FIG. 7. Crystal structure of the Z,Z-2PyDIG·$HBPh_4$ photoisomer. Red spheres are oxygen atoms, blue spheres are nitrogen atoms, black spheres are carbon atoms, magenta spheres are boron atoms, and white spheres are hydrogen atoms. Disordered solvent molecules have been removed for clarity. Intramolecular NH . . . N hydrogen bonds are depicted as dotted lines.

As hypothesized, the structure of the photoisomerized 2PyDIG reveals the Z,Z configuration and stabilizing intramolecular hydrogen bonds to the pyridine N atoms (FIG. 7). Although the unsymmetrical conformer shown was observed in the crystal instead of the symmetrical one depicted in FIG. 1, the guanidine hydrogen atoms engaged in hydrogen bonds with pyridine N atoms are presumably inaccessible for anion binding. Accordingly, attempts to crystallize the Z,Z photoisomer with various oxyanions ($SO_4^{2-}$, $NO_3^-$, $ReO_4^-$, $ClO_4^-$, and p-toluenesulfonate) were not successful. However, Z,Z-2PyDIG could be crystallized from methanol using a large, non-coordinating anion, tetraphenylborate, before the cation underwent thermal relaxation. The rotation about one central guanidine C—N bond was not entirely expected because of the presumed loss of one intramolecular hydrogen bond from the —$NH_2$ group to the imine N atom, but DFT analysis shows a negligible energy difference between the two geometric isomers. The isomer maintains planarity upon conversion, while the stabilizing intramolecular hydrogen bonds between the N—H guanidinium protons and pyridine N atoms have measured contact distances of 1.971 and 1.969 Å. Hydrogen bonding between guanidinium —$NH_2$ protons and solvent molecules is also present in the crystal packing, as well as π-stacking between 2PyDIG pyridine rings, with distance between centroids of 3.60 Å and a slippage angle of 21.9°.

Sulfate Binding by the E,E-2PyDIG Cation

Figure 8A:
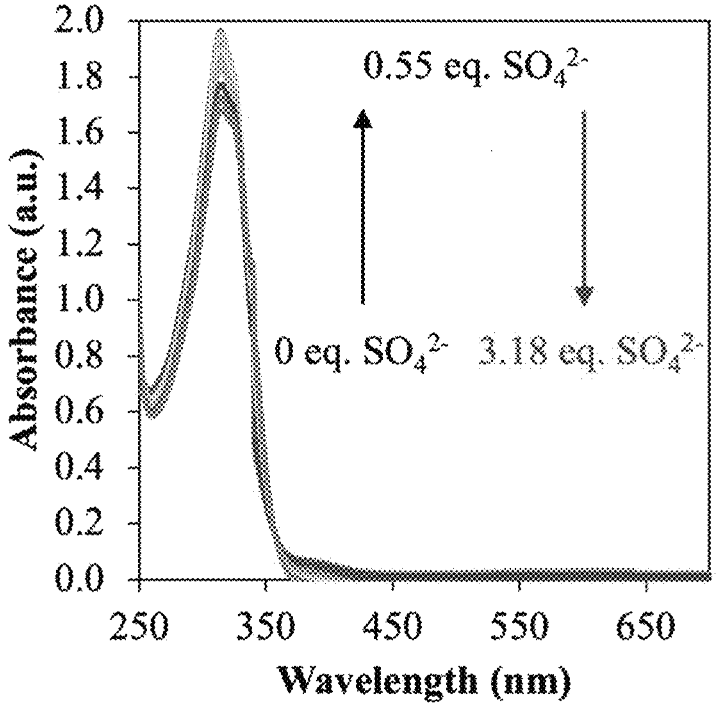
FIGS. 8A-8B. Absorbance (FIG. 8A) and speciation plot (FIG. 8B) of the UV-Vis titration of E,E-2PyDIG·HOTf with tetramethylammonium sulfate relative to 2PyDIG·HOTf in DMSO-$d_6$ at 24° C. Here, BH represents the monoprotonated cationic form of 2PyDIG.
Figure 8B:
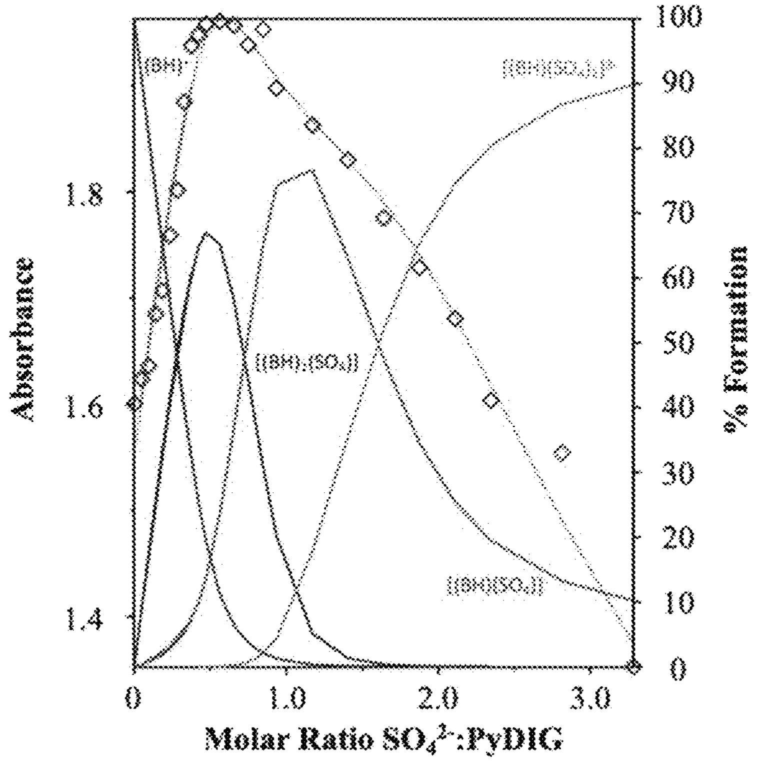

UV-vis absorption spectroscopy reveals the E,E-2PyDIG cation binds sulfate very strongly in DMSO-$d_6$. Titration of a 1 mM solution of E,E-2PyDIG·HOTf with tetramethylammonium sulfate results in a change in the intensity at the absorption maximum (FIGS. 8A and 8B). The absorbance maximum at 315 nm increases approximately 25% in the range 0 to 0.5 mole ratio sulfate:2PyDIG, followed by a 65% decrease in absorbance from 0.5 to 3.0 mole ratio. The change in absorbance is attributed to sulfate binding via hydrogen bonding, as found in the crystal structure, ruling out proton transfer observed elsewhere in the presence of basic anions such as fluoride. If this were the case, a transition at 376 nm would arise from the neutral 2PyDIG receptor. The titration was repeated and analyzed three times, with the profiles of absorbance values as a function of sulfate-to-receptor mole ratio showing the same features in all three trials. A three-species complexation model is required to fit the data, assuming free E,E-2PyDIG cation and sulfate anion as reactant species. In the titration of sulfate into the receptor solution, the first complex that appears has the same stoichiometry as found in the crystal structure (FIG. 6), $[(2PyDIG)_2(SO_4)]$, which indicates this 2:1 complex is highly stable. Above a sulfate-to-receptor mole ratio of 0.5, further addition of sulfate generates the 1:1 complex $[(2PyDIG)(SO_4)]$, which apparently adds an additional sulfate to give the $[(2PyDIG)(SO_4)_2]$ complex past a sulfate-to-receptor mole ratio of 1.0. Table 1 (below) summarizes the averaged binding constants and the corresponding formation equilibria (Eqs. 2-4).

Parallel $^1H$ NMR titrations in DMSO-$d_6$ produce statistically identical results as found by UV-vis titrations (Table 1). Titration of a 1 mM solution of E,E-2PyDIG HOTf with tetramethylammonium sulfate results in small but consistently measurable downfield shifts (Δδ=0.04 ppm, of the guanidinium N—H protons. The observed change in chemical shift, while minor, is not uncommon in hydrogen-bonding anion-binding systems. While the small change in chemical shift may seem at odds with the large binding constants determined, it may be, as found previously with sulfate binding by guanidinium receptors in competitive hydrogen-bonding solvents, that the anion binding may be entropy-driven due to significant solvent interactions and reorganizations (M. Berger et al., *Angew. Chem. Int. Ed.,* 37(19), 2694-2696, 1998). Although the iminoguanidinium group is weakly acidic, with typical $pK_a$ values in the range of 7-9, the $^1H$ NMR spectrum of the neutral E,E-2PyDIG isomer does not match the spectrum obtained in the titration of E,E-2PyDIG cation with sulfate, thus ruling out deprotonation during titration. The titration was repeated and analyzed four times. Again, a three-species complexation model had to be employed to fit the data. The speciation profiles of chemical shifts as a function of sulfate-to-receptor mole ratio show the same features in the four trials and follow a similar trend observed in the UV-vis titrations. Upon addition of sulfate into the 2PyDIG solution, the first complex that appears again is the $[(2PyDIG)_2(SO_4)]$ at a sulfate-to-receptor mole ratio of 0.5, also reported with absorption-based titrations. Further addition of sulfate generates the 1:1 complex [(2PyDIG)($SO_4$)], at 1.0 sulfate to receptor ratio. An additional sulfate gives the [(2PyDIG)($SO_4$)$_2$] complex beyond a sulfate-to-receptor mole ratio of 1.0.

TABLE 1

Comparison of fitted sulfate-binding constants corresponding to formation equilibria 2-4 obtained from the $^1$H NMR and UV-vis titrations.[a]

| Equilibrium | Eq. | Constant | E,E NMR Value[b] | E,E UV Value[c] |
|---|---|---|---|---|
| (E,E-2PyDIG)$^+$ + $SO_4^{2-}$ ⇌ [(E,E-2PyDIG)($SO_4$)] | (2) | log $b_{11}$ | 7.40 ± 0.92 | 7.21 ± 0.48 |
| 2(E,E-2PyDIG)$^+$ + $SO_4^{2-}$ ⇌ [(E,E-2PyDIG)$_2$($SO_4$)] | (3) | log $b_{21}$ | 11.67 ± 0.95 | 11.25 ± 0.68 |
| (E,E-2PyDIG)$^+$ + $SO_4^{2-}$ ⇌ [(E,E-2PyDIG)($SO_4$)$_2$]$^{3-}$ | (4) | log $b_{12}$ | 12.23 ± 1.18 | 11.70 ± 0.95 |

[a]In each titration, tetramethylammonium sulfate was added to ca. 1 mM 2PyDIG•HOTf in DMSO-$d_6$ at 24° C.
[b]Average of four titration measurements.
[c]Average of three titration measurements. Uncertainty for each value as shown represents the precision of the four trials; the standard error of the mean can be obtained by dividing by the square root of the number of replicates. Constants shown are concentration quotients.

In comparison to published binding constants, E,E-2PyDIG cation binds sulfate with comparable if not superior strength. Values for the binding constants as an average of the UV-vis and NMR experiments are shown in Table 2 (below). The 1:1 and 2:1 binding constants of 7.25±0.43 (log $b_{11}$) and 11.39±0.55 (log $b_{21}$) shown in Table 2 may be the highest recorded for a monofunctional guanidinium receptor in a polar medium (e.g., M. Berger, Ibid.). The highest comparable sulfate binding was reported by Kobiro and Inoue (*J. Am. Chem. Soc.*, 125(2), 421-427, 2003) for a receptor containing 4-(N,N-dimethylamino)benzoate group tethered to a bicyclic guanidinium subunit. This receptor forms 1:1 and 2:1 adducts with sulfate with stepwise binding constants of $1.53 \times 10^6 M^{-1}$ and $4.84 \times 10^4 M^{-1}$ in $CD_3CN$, respectively, corresponding to log $b_n$ and log $b_{21}$ values of 6.18 and 10.86. Although these values are approximately an order of magnitude lower than those shown in Table 2 for E,E-2PyDIG, within the precision of the present measurements, the values are statistically comparable. However, DMSO possesses strong electron-pair donor strength compared with $CH_3CN$ and therefore would solvate E,E-2PyDIG more strongly by accepting hydrogen bonds, thereby competing with anion binding. Due to this solvation-based competition effect, the superior sulfate binding strength of E,E-2PyDIG is likely to be real. The strength of the E,E-2PyDIG cation in binding sulfate may be attributed to the greater acidity of the iminoguanidininum group. While guanidinium cations are very weakly acidic in water (pKa=13.6), iminoguanidinium cations are several orders of magnitude more acidic, sufficient to dissociate under near-neutral conditions ($pK_a$ values of 7-9). Thus, in the absence of proton transfer (ruled out here, vide supra), the hydrogen-bond-donor strength of the receptor is maximized.

With larger amounts of sulfate added to E,E-2PyDIG, the fitting indicates the formation of a 1:2 adduct with a log $b_{12}$ of 11.91±0.74 $M^{-1}$ (Table 2). This putative addition of the second sulfate to the 1:1 adduct is surprisingly strong (log $K_{12}$=4.7±1.5), given the negative charge of the 1:1 complex and competition for hydrogen bonding by the first sulfate. Without being bound by theory, a possible explanation is that the tetramethylammonium cations present may be moderating the coulombic repulsion. At E,E-2PyDIG concentrations greater than 1 mM in DMSO, a precipitation reaction begins at a sulfate:E,E-2PyDIG mole ratio of 2, which prevents carrying out titrations at higher concentrations of E,E-2PyDIG.

Sulfate Binding by the Z,Z-2PyDIG Cation

Figure 9A:
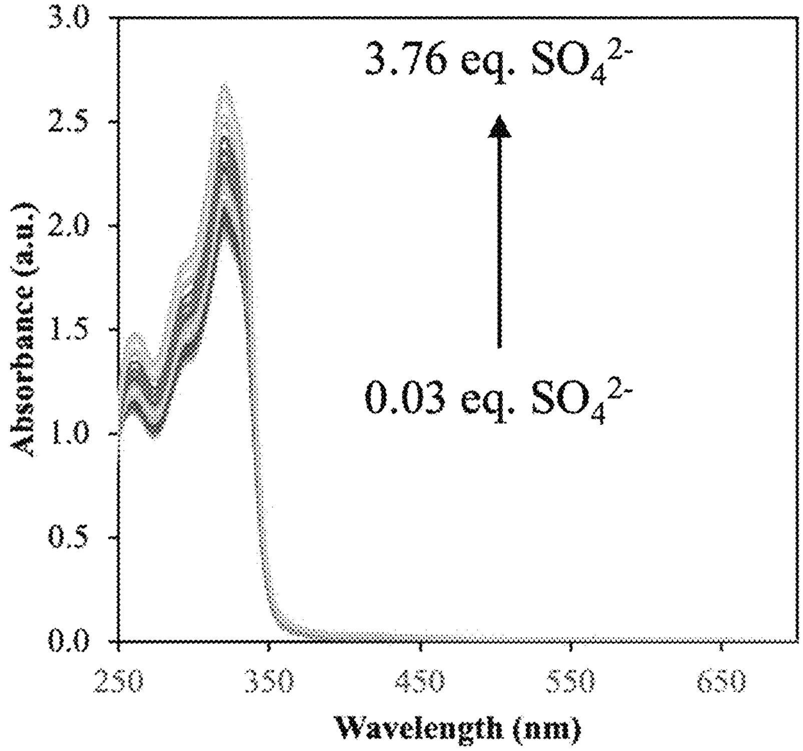
FIGS. 9A-9B. Absorbance (FIG. 9A) and speciation plot (FIG. 9B) of the UV-Vis titration of E,E-2PyDIG·HOTf with tetramethylammonium sulfate relative to 2PyDIG·HOTf in DMSO-$d_6$ at 24° C. Here, BH represents the monoprotonated cationic form of 2PyDIG.
Figure 9B:
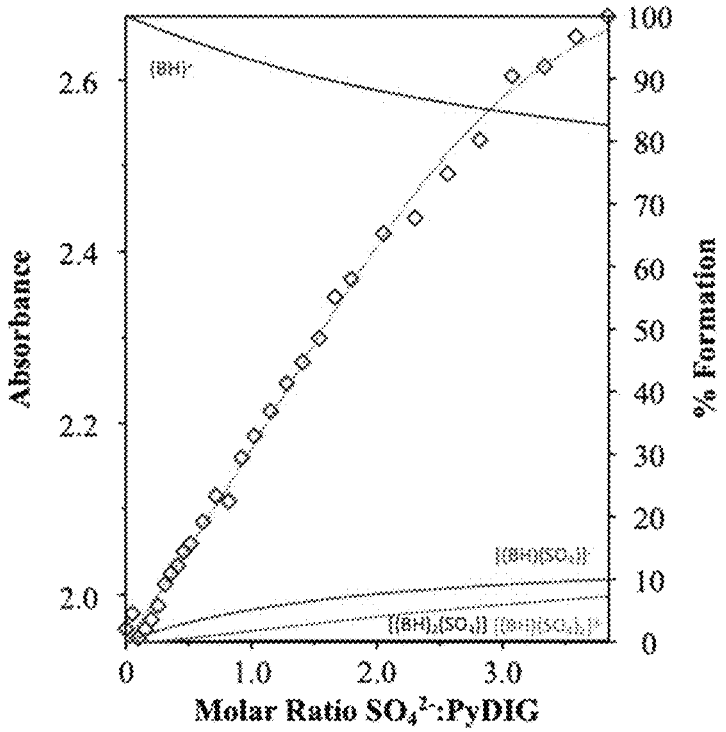

Photoisomerization to the Z,Z-2PyDIG isomer results in a marked decrease in sulfate binding. Under the same conditions used for the titrations of the E,E isomer, the $^1$H NMR spectra of 1.1 mM Z,Z-2PyDIG in DMSO-$d_6$ (after 2 h irradiation of the E,E isomer) show no measurable changes in chemical shifts upon addition of tetramethyl ammonium sulfate. However, a significant interaction can be quantified in the UV-vis spectra in DMSO-$d_6$ through the Z,Z isomer's absorption maximum at 320 nm, which increases in intensity with the addition of sulfate (FIGS. 9A and 9B). The same speciation model used for the E,E titrations was again needed to adequately fit the data. Binding constants averaged over three titrations are given in Table 2. Slight deviations from the model are observed at low sulfate-to-receptor mole ratio (<0.03), consistent with the minor amount of unconverted E,E-2PyDIG remaining in solution, which out-competes the Z,Z form for sulfate binding until the minor amount of E,E isomer is consumed. Effectively, if a small amount of E,E isomer remains in the Z,Z solutions after photoirradiation, that amount being on the order of 0.03 mM in the present experiments, represents the lower limit of sulfate that can be regulated by photoirradiation.

TABLE 2

Comparison of sulfate binding constants for E,E and Z,Z isomers of 2PyDIG.

| Equilibrium | Eq. | Constant | E,E[a] Avg Value[b] | Z,Z[b] UV Value[c] | E,E − Z,Z Difference |
|---|---|---|---|---|---|
| (2PyDIG)$^+$ + $SO_4^{2-}$ ⇌ [(2PyDIG)($SO_4$)]$^-$ | (2) | log $b_{11}$ | 7.25 ± 0.43 | 1.85 ± 0.15 | 5.40 ± 0.45 |
| 2(2PyDIG)$^+$ + $SO_4^{2-}$ ⇌ [(2PyDIG)$_2$($SO_4$)] | (3) | log $b_{21}$ | 11.39 ± 0.55 | 3.08 ± 0.09 | 8.31 ± 0.56 |
| (2PyDIG)$^+$ + $SO_4^{2-}$ ⇌ [(2PyDIG)($SO_4$)$_2$]$^{3-}$ | (4) | log $b_{12}$ | 11.91 ± 0.74 | 4.00 ± 0.19 | 7.91 ± 0.76 |

[a]Precision-weighted average of the values shown in Table 1 for the constants shown for UV-vis and NMR titrations.
[b]Average of three titrations (see SI) in which tetramethylammonium sulfate was added to ca. 1 mM Z,Z-2PyDIG•HOTf in DMSO-$d_6$ at 24° C. following 2 h irradiation of the initial E,E isomer. Uncertainty for each value as shown represents the precision of the three trials; the standard error of the mean can be obtained by dividing by the square root of the number of replicates. Constants shown are concentration quotients.

2PyDIG Photoswitching in the Presence of Sulfate

Photoisomerization of E,E-2PyDIG in the presence of sulfate does not affect the efficiency of photoisomerization to the Z,Z isomer; however, a near quantitative thermal relaxation to the E,E isomer was observed. A solution of ca. 10 mM 2PyDIG·HOTf in DMSO-$d_6$ was monitored by $^1$H NMR spectroscopy. After addition of 0.5 mol ratio of sulfate to E,E-2PyDIG before irradiation, the relative E,E to Z,Z ratios remain unchanged according to $^1$H NMR (93.1±1.2% and 92.8±1.4% E,E, before and after sulfate addition, respectively), accompanied with a slight downfield shift of the NH guanidine protons (Δδ=0.02 ppm). After 2 hours of UV irradiation, the remaining 32.5±3.8% E,E isomer at PSS as compared with 32.3.±4.4% E,E isomer at PSS in the absence of sulfate suggests that the sulfate anion does not play a controlling role in the photoisomerization process. Thermal relaxation from PSS was monitored at 50° C. in the presence of sulfate, with thermal equilibrium returning to 91.2±1.4% E,E isomer after 36 hours with no further change at 60 hours, almost to the pre-irradiation state. This process was repeated upon addition of 0.5 and 1.0 mol ratio sulfate post-irradiation, with similar PSS and thermal equilibrium states being achieved compared with sulfate addition pre-irradiation (Table 3 below). The expected near-complete reversion to the E,E isomer reflects the driving force of sulfate binding by the E,E isomer (Eq. 5). In a catch-and-release cycle, the more complete reversion to the E,E isomer in the dark effectively represents an increase in capacity.

TABLE 3

Relative degree of isomerization of E,E-2PyDIG$^+$ in the absence or presence of sulfate during photoisomerization and thermal relaxation.

Figure 10:
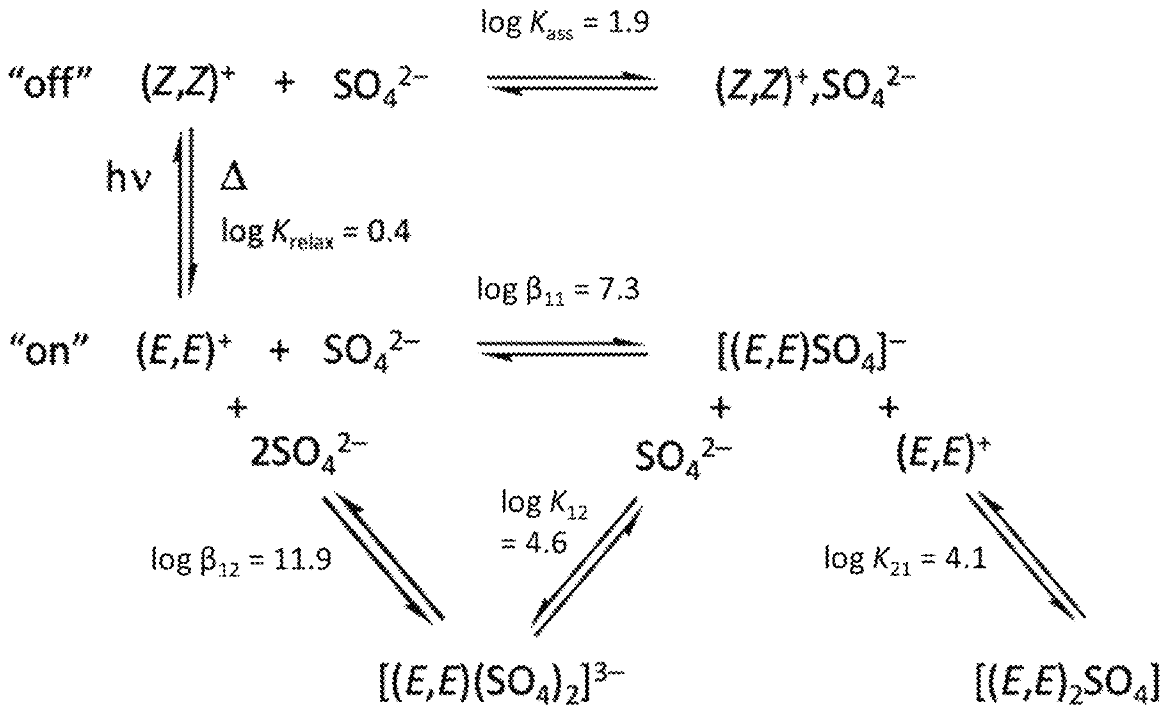
FIG. 10. Schematic showing photoisomerization and associated sulfate-binding equilibria in the 2PyDIG system as characterized in DMSO-$d_6$.

| | Relative Amount of E,E-2PyDIG$^+$ (%) | | | |
|---|---|---|---|---|
| | Control; no $SO_4^{2-}$ added | $SO_4^{2-}$ added before irradiation | $SO_4^{2-}$ added after irradiation | $SO_4^{2-}$ added after irradiation |
| Mol ratio $SO_4^{2-}$:2PyDIG$^+$ | 0 | 0.5 | 0.5 | 1.0 |
| Before irradiation | 97.4 ± 0.6 | 91.1 ± 1.2% | 95.1 ± 1.4 | 93.4 ± 2.9 |
| After irradiation | 32.3 ± 4.4 | 32.5 ± 3.8 | 33.2 ± 5.3 | 31.0 ± 4.7 |
| Thermal equilibrium | 70.5 ± 0.9 | 91.2 ± 1.4 | 93.1 ± 3.3 | 91.6 ± 1.9 |

used in the titration of E,E-2PyDIG with sulfate, no observable change in any chemical shift of Z,Z-2PyDIG, including the N—H iminoguanidinium protons, could be detected with $^1$H NMR upon titration of sulfate, while a change in the absorption maximum is observed with absorption spectroscopy. As indicated in the crystal structure (FIG. 6), the single N—H groups engage in intramolecular hydrogen bonding to the pyridyl nitrogen atoms. Although no direct interaction of the iminoguanidinium N—H groups of Z,Z-2PyDIG with sulfate is evident by $^1$H NMR, Z,Z-2PyDIG likely does associate partially with sulfate in solution electrostatically. It can be estimated from the Bjerrum model that the 2PyDIG cation (either isomer) is partially ion-paired under the conditions of the experiments reported herein. The estimated $K_{ass}$ of 2.95 for 2PyDIG and sulfate implies approximately 36% of the receptor is associated with sulfate. Thus, the large binding constants for the E,E isomer may be thermodynamically driven by hydrogen bonding likely assisted by entropy, while the interaction evident by UV-vis spectral changes of the Z,Z isomer upon sulfate addition are taken to be largely electrostatic in origin. The system of reactions involved is shown schematically in FIG. 10.

DFT Calculations

Figure 11:
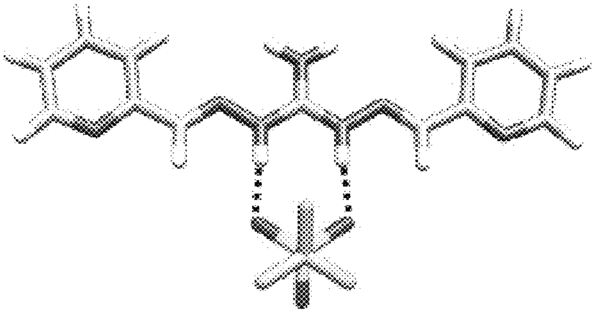
FIG. 11. Structures and relative free energies (kcal/mol) of the E,E- and Z,Z-forms of 2PyDIG with the triflate anion optimized in the solvent reaction field (DMSO) at the B3LYP/def 2TZVPP level, with single-point energy corrections using the DLPNO-CCSD(T)/cc-pVTZ theory.
Figure 11:
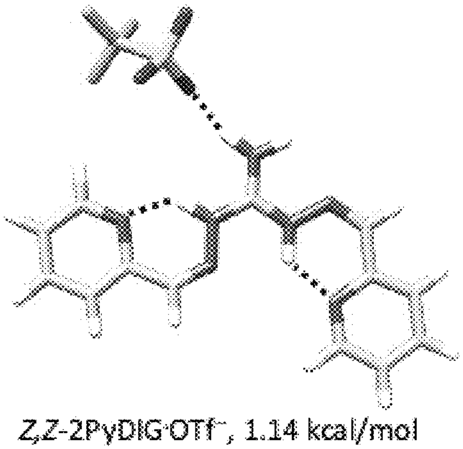

Corroborating calculations on bare 2PyDIG rotamers and the interaction of triflate with 2PyDIG were performed at the B3LYP/def2TZVPP level of theory, with higher energy corrections computed using the DLPNO-CCSD(T)/cc-pVTZ theory (W. B. Scheider et al., *J. Chem. Theory Comput.*, 12(10), 4778-4792, 2016). It was observed that the gas-phase complex with the E,E-isomer remains stable during optimization in the implicit solvent reactive field, but the complex with the Z,Z-isomer undergoes a structural change, as a hydrogen bond between the NH group and triflate in the gas phase is completely lost in the solvent, showing only a weak hydrogen bond between much less acidic guanidinium $NH_2$ group and triflate (FIG. 11). A loss of one hydrogen bond from the guanidinium NH group in the Z,Z form is also reflected in the relative free energies of the E,E- and Z,Z-forms, with the latter being more stable with no anion, but less stable in the presence of a weakly coordinating anion (FIG. 11). The computed free energy difference between the two forms in the presence of triflate at 25° C. is 1.1 kcal/mol, in good agreement with the experimental value of 0.5 kcal/mol (Eq. 1). This further supports the dramatic decrease in the anion binding affinity upon photoconversion, corroborating the nonbinding behavior of the closed Z,Z form.

$$[\text{E,E-2PyDIG}]^+ \xrightarrow{SO_4^{2-}} \begin{matrix}[(\text{E,E-2PyDIG})(SO_4)]^- \\ + \\ [(\text{E,E-2PyDIG})_2(SO_4)]\end{matrix} \underset{\Delta}{\overset{hv}{\rightleftharpoons}} [\text{Z,Z-2PyDIG}]^+ + SO_4^{2-} \qquad (5)$$

Photoswitching of Sulfate Binding

Figure 12:
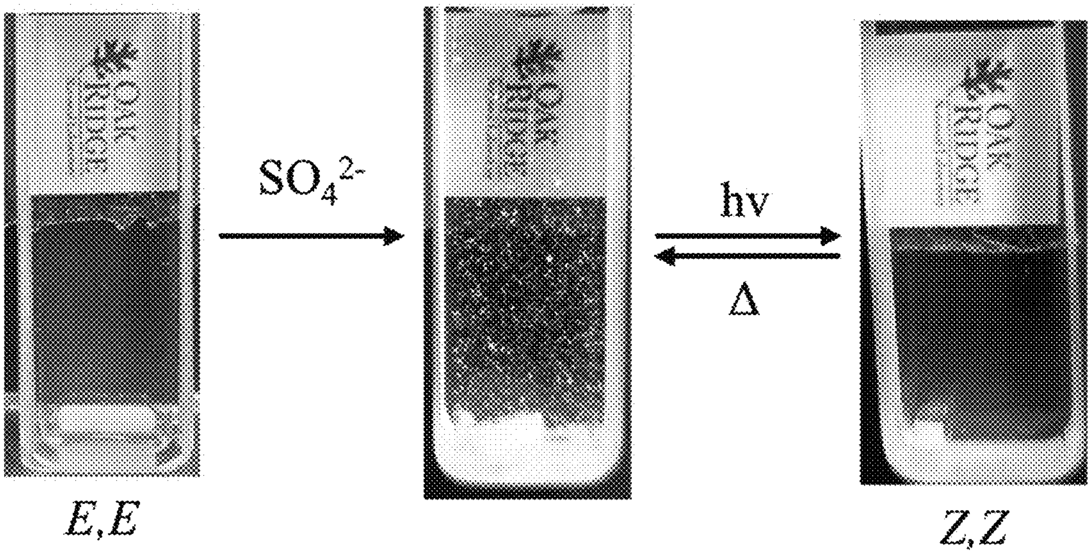
FIG. 12. Photographic schematic of sulfate precipitation-redissolution cycling using 2PyDIG. A solution of 10 mM E,E-2PyDIG·HOTf in DMSO (left), precipitated $[(E,E\text{-}2PyDIG)(SO_4)_2]^{3-}$ upon addition of 2 equivalents of sulfate as tetramethylammonium salt (middle). The precipitate redissolved after UV irradiation (right).

Dramatic switched-off sulfate binding occurs upon photoisomerization of E,E-2PyDIG into the Z,Z isomer, as determined by $^1$H NMR and UV-vis absorption spectroscopies in DMSO-$d_6$. As shown in the difference column of Table 2, the initially strong binding strength of 2PyDIG upon photoirradiation of its E,E isomer to the Z,Z isomer practically vanishes. Comparing the 1:1 binding constants, the difference 5.40±0.45 represents a decrease exceeding five orders of magnitude. Without being bound by theory, the low binding affinity of the Z,Z isomer of 2PyDIG may be attributed to the hypothesized inaccessibility of the two single N—H binding protons of the guanidinium core, which become involved in internal hydrogen bonding to the neighboring pyridine N atoms. Under the same conditions A Photoswitched Sulfate Precipitation-Dissolution Cycle Excess sulfate precipitates with E,E-2PyDIG and redissolves with photoirradiation, demonstrating a rudimentary, proof-of-concept binding-release cycle. At higher concentrations in DMSO, the 2PyDIG receptor binds to sulfate as the 1:2 complex (Eq. 4 in Table 1) and precipitates as illustrated in FIG. 12. The precipitate instantly forms upon addition of two equivalents of sulfate, putatively assigned as the $[(\text{E,E-2PyDIG})(SO_4)_2]^{2-}$ species. Attempts to obtain crystals suitable for X-ray crystallography have so far proven difficult due to the fast rate of the precipitation; however, addition of 0.5 and 1 equivalents of sulfate does not lead to solid formation, suggesting the solid is the 1:2 complex containing tetramethylammonium counterions. The present work was able to indirectly determine the amount of precipitated 2PyDIG and relative ratio of PyDIG to sulfate of the precipitate. Upon addition of sulfate to the E,E-2PyDIG solution, 73.7% of the E,E-PyDIG receptor precipitates according to a $^1$H NMR spectrum of the supernatant. Adding barium chloride to the separated supernatant precipitated the non-interacting sulfate, affording a ratio of sulfate to PyDIG of 2.05. The estimated percentage of sulfate precipitated by gravimetric analysis is 63%. Photoirradiating the suspension redissolves the solid, where the E,E-PyDIG undergoes photoisomerization to the Z,Z form, ejecting bound sulfate in the process, as summarized in Eq. 6. Over time, the free Z,Z-PyDIG in solution reverts to the E,E through a thermal relaxation process, where the $[(E,E\text{-}2PyDIG)(SO_4)_2]^{3-}$ species is again precipitated.

CONCLUSIONS

The present work demonstrates that photoisomerization of the E,E isomer to the Z,Z isomer occurs efficiently in DMSO-$d_6$ induced by UV light, as monitored by $^1$H NMR and UV-vis absorption spectroscopies. At low concentrations that minimize the apparently bimolecular relaxation process, the photoconversion to the Z,Z form is nearly quantitative at 95.6±0.4%, exceeding previously reported conversion efficiencies among photoswitchable anion receptors. Intramolecular hydrogen bonding of the guanidinium N—H groups to the pyridines stabilizes the Z,Z isomer, as evidenced by DFT computations and crystal structures of the binding E,E isomer with sulfate and the nonbinding Z,Z photoisomer. The exceptional binding of sulfate by the E,E isomer, involving 1:1, 2:1, and 1:2 receptor:sulfate species, is at least as strong, and likely much stronger, than previously reported monofunctional guanidinium receptors. Possessing a relatively low $pK_a$ among anion receptors, 2PyDIG exhibits exceptionally strong anion binding via hydrogen bonding that verges on proton transfer. This strong binding of sulfate is diminished by more than five orders of magnitude upon photoisomerization to the Z,Z form. Thus, both the E,E-Z,Z photoisomerization and the photoswitching of binding and release are exceptionally efficient, and they can be demonstrably exploited for light-driven phase change as shown by the reversible precipitation of the 1:2 complex.

While there have been shown and described what are at present considered the preferred embodiments of the invention, those skilled in the art may make various changes and modifications which remain within the scope of the invention defined by the appended claims.

What is claimed is:

1. A compound having the following structure:

(1a)

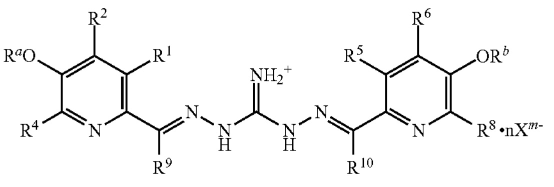

wherein:

$R^1$, $R^2$, $R^4$, $R^5$, $R^6$, and $R^8$ are hydrogen atom;

$R^9$ and $R^{10}$ are independently selected from hydrogen atom and methyl;

$X^{m-}$ is an anionic species with a magnitude of charge m, where m is an integer of at least 1;

$R^a$ and $R^b$ are linear or branched alkyl or alkenyl groups containing 1-30 carbon atoms; and n is a number, provided that n×m=1.

2. The compound of claim 1, wherein $R^9$ and $R^{10}$ are hydrogen atoms.

3. The compound of claim 1, wherein $X^{m-}$ is a halide.

4. The compound of claim 1, wherein $X^{m-}$ is an oxyanion.

5. A method for removing an oxyanion from a liquid source, the method comprising contacting said liquid source with an oxyanion precipitating compound having the following structure:

(1)

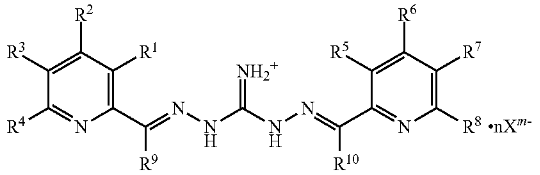

or (2)

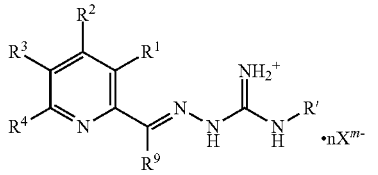

to result in precipitation of a salt of said oxyanion precipitating compound and oxyanion;

wherein:

$R^1$, $R^2$, $R^3$, $R^4$, $R^5$, $R^6$, $R^7$, $R^8$, $R^9$, and $R^{10}$ are independently selected from (i) hydrogen atom, (ii) hydrocarbon groups (R) containing 1-30 carbon atoms and optionally substituted with one or more fluorine atoms, (iii) —OR' groups, (iv) —NR'$_2$ groups, (v) —C(O) R' groups, and (vi) halogen atoms, wherein R' groups are independently selected from R groups and hydrogen atoms;

at least one of $R^1$, $R^2$, $R^3$, and $R^4$ in Formula (2) is selected from groups (iii)-(vi) provided above;

$X^{m-}$ is an anionic species with a magnitude of charge m, where m is an integer of at least 1, provided that $X^{m-}$ is an anionic species exchangeable with the oxyanion in said liquid source before said oxyanion precipitating compound contacts said liquid source, and $X^{m-}$ is said oxyanion in said salt; and n is a number, provided that n×m=1.

6. The method of claim 5, wherein said oxyanion is selected from the group consisting of sulfate, nitrate, selenate, tellurate, phosphate, arsenate, carbonate, bicarbonate, perchlorate, and metal oxyanions.

7. The method of claim 5, wherein said oxyanion is sulfate or phosphate.

8. The method of claim 5, wherein $X^{m-}$ is halide or nitrate before said oxyanion precipitation compound contacts said liquid source.

9. The method of claim 5, wherein the oxyanion precipitating compound has the structure of Formula (1).

10. The method of claim 9, wherein $R^9$ and $R^{10}$ are hydrogen atoms.

11. The method of claim 9, wherein at least one of $R^1$, $R^2$, $R^3$, $R^4$, $R^5$, $R^6$, $R^7$, $R^8$, $R^9$, and $R^{10}$ is selected from R, —OR', —NR'$_2$, and —C(O)R'.

12. The method of claim 9, wherein at least one of $R^1$, $R^2$, $R^3$, $R^4$, $R^5$, $R^6$, $R^7$, and $R^8$ is an —OR' group.

13. The method of claim 12, wherein the compound has the following structure:

(1a)

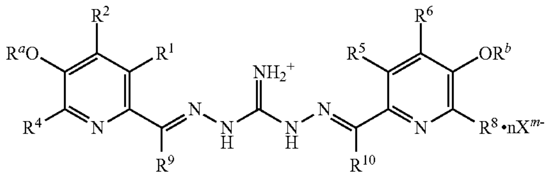

wherein $R^1$, $R^2$, $R^4$, $R^5$, $R^6$, $R^8$, $R^9$, and $R^{10}$ are as defined in claim 1, and $R^a$ and $R^b$ are linear or branched alkyl or alkenyl groups containing 1-30 carbon atoms.

14. The method of claim 9, wherein, following precipitation of the salt, the salt is removed from the liquid source, transferred to a second liquid, and the salt is exposed to electromagnetic radiation in the second liquid to isomerize the compound of Formula (1) to a closed (Z,Z) form having the following structure:

(1')

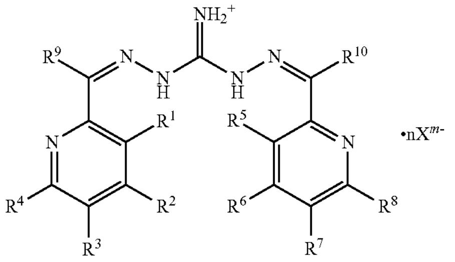

with simultaneous release of the oxyanion and dissolution of an uncomplexed form of the closed oxyanion precipitating compound according to Formula (1') in the second liquid or partitioning of an uncomplexed form of the closed oxyanion precipitating compound according to Formula (1') in a third liquid in contact with the second liquid.

15. The method of claim 14, wherein the uncomplexed form of the closed oxyanion precipitating compound is thermally converted back to the structure of Formula (1).

16. The method of claim 15, wherein, after thermal conversion, the oxyanion precipitating compound of Formula (1) is re-used in a subsequent process of removing an oxyanion from a liquid source.

17. The method of claim 14, wherein the electromagnetic radiation has a wavelength below 600 nm.

18. The compound of claim 1, wherein $R^a$ and $R^b$ are linear or branched alkyl or alkenyl groups containing 2-30 carbon atoms.

19. The compound of claim 1, wherein $R^a$ and $R^b$ are linear or branched alkyl or alkenyl groups containing 3-30 carbon atoms.

* * * * *